US008343450B2

(12) United States Patent
Wang

(10) Patent No.: US 8,343,450 B2
(45) Date of Patent: Jan. 1, 2013

(54) FUNCTIONALIZED CARBON NANOTUBES, RECOVERY OF RADIONUCLIDES AND SEPARATION OF ACTINIDES AND LANTHANIDES

(75) Inventor: Pingshan Wang, Hudson, OH (US)

(73) Assignee: Chemnano Materials, Ltd., Hudson, OH (US)

( * ) Notice: Subject to any disclaimer, the term of this patent is extended or adjusted under 35 U.S.C. 154(b) by 354 days.

(21) Appl. No.: 12/287,368

(22) Filed: Oct. 8, 2008

(65) Prior Publication Data
US 2009/0093664 A1    Apr. 9, 2009

Related U.S. Application Data

(60) Provisional application No. 60/998,005, filed on Oct. 9, 2007, provisional application No. 60/998,872, filed on Oct. 12, 2007.

(51) Int. Cl.
*D01F 9/12*    (2006.01)
*G21F 9/06*    (2006.01)
*C07F 9/54*    (2006.01)
*C07C 237/00*  (2006.01)
*C07D 323/00*  (2006.01)
*C07D 213/22*  (2006.01)

(52) U.S. Cl. .................. 423/447.1; 977/745; 977/754; 977/847; 588/18; 564/15; 564/153; 549/349; 546/257

(58) Field of Classification Search .... 423/447.1–447.3, 423/445 B; 977/742–754, 842–848; 428/367; 588/18; 564/15, 153; 549/349; 546/257
See application file for complete search history.

(56) References Cited

U.S. PATENT DOCUMENTS
4,235,943 A    11/1980   McComas et al.
(Continued)

FOREIGN PATENT DOCUMENTS
WO    WO 94/24138 A1    10/1994
(Continued)

OTHER PUBLICATIONS

Nakayama-Ratchford, et al., Noncovalent Functionalization of Carbon Nanotubes by Fluorescein-Polyethylene Glycol: Supramolecular Conjugates with pH-Dependent Absorbance and Fluorescence, J. Am. Chem. Soc. 2007; 129: 2448-2449 (published online Feb. 7, 2007).*

(Continued)

*Primary Examiner* — Daniel C. McCracken
(74) *Attorney, Agent, or Firm* — Hudak, Shunk & Farine Co. LPA

(57) ABSTRACT

Methods and compositions to extract radionuclides such as various actinides and lanthanides from organic and/or aqueous solutions by utilizing extractant functionalized carbon nanotubes are disclosed. More particularly, phosphorous-containing (such as phosphine oxides, phosphoric acids or phosphates) organic extractants and other predesigned extractants (such as crown ethers, calncrown derivatives, malonamide and diglycolamide derivatives, polyethylene glycol derivatives, cobalt dicarbollide derivatives, and N-donating heterocyclic ligands) can be covalently and/or non-covalently employed on the surfaces and/or ends (tips) of carbon nanotubes for the purpose of removal radionuclides such as various actinides and lanthanides from organic and/or aqueous solutions. Extractant functionalized carbon nanotubes can be used for extracting radioactive nuclides from nuclear waste or spent nuclear fuel, which are produced and/or reprocessed from the nuclear power generation or other nuclear application.

16 Claims, 4 Drawing Sheets

U.S. PATENT DOCUMENTS

| | | | |
|---|---|---|---|
| 4,548,790 | A | 10/1985 | Horwitz et al. |
| 4,574,072 | A | 3/1986 | Horwitz et al. |
| 5,468,456 | A | 11/1995 | Nunez et al. |
| 6,258,333 | B1 | 7/2001 | Romanovskiy et al. |
| 6,270,737 | B1 | 8/2001 | Zaitsev et al. |
| 6,312,653 | B1 | 11/2001 | Delmau et al. |
| 6,502,767 | B2 | 1/2003 | Kay et al. |
| 6,722,584 | B2 | 4/2004 | Kay et al. |
| 6,736,902 | B2 | 5/2004 | Tefft et al. |
| 6,843,921 | B2 | 1/2005 | Kuraoka et al. |
| 6,845,929 | B2 | 1/2005 | Dolatabadi et al. |
| 6,915,964 | B2 | 7/2005 | Tapphorn et al. |
| 2002/0110513 | A1 | 8/2002 | Margrave et al. |
| 2002/0168466 | A1 | 11/2002 | Tapphorn et al. |
| 2003/0008772 | A1* | 1/2003 | Ma et al. ............ 502/180 |
| 2003/0233979 | A1 | 12/2003 | Tefft et al. |
| 2004/0146560 | A1 | 7/2004 | Whiteford et al. |
| 2005/0006623 | A1* | 1/2005 | Wong et al. ............ 252/70 |
| 2006/0021938 | A1 | 2/2006 | Diallo |
| 2006/0051290 | A1 | 3/2006 | Wilson et al. |
| 2006/0081174 | A1 | 4/2006 | Baran |
| 2006/0204738 | A1 | 9/2006 | Dubrow et al. |
| 2006/0205920 | A1* | 9/2006 | Dozol et al. ............ 528/398 |
| 2006/0231399 | A1 | 10/2006 | Smalley et al. |
| 2006/0251568 | A1 | 11/2006 | Fahlman |
| 2007/0243335 | A1 | 10/2007 | Belaschchenko |

FOREIGN PATENT DOCUMENTS

| | | | |
|---|---|---|---|
| WO | WO 2006/002341 | * | 1/2006 |
| WO | WO2007/054313 A1 | | 5/2007 |
| WO | WO2007/110134 A1 | | 10/2007 |
| WO | WO2008/031185 A1 | | 3/2008 |
| WO | WO2008/073110 A1 | | 6/2008 |
| WO | WO2008/098336 A1 | | 8/2008 |

OTHER PUBLICATIONS

Guldi, et al., Multifunctional molecular carbon materials—from fullerenes to carbon nanotubes, Chem. Soc. Rev. 2006; 35: 471-487.*

S. Campidelli et al., Dendrimer-Functionalized Single-Wall Carbon Nanotubes: Synthesis, Characterization, and Photoinduced Electron Transfer, J. Am. Chem. Soc., 2006, vol. 128, pp. 12544-12552, published on Web Sep. 6, 2006 by American Chemical Society.

SH Hwang et al., Dendron-Tethered and Templated CdS Quantum Dots on Single-Walled Carbon Nanotubes, J. Am. Chem. Soc., 2006, vol. 128, pp. 7505-7509, published on Web May 23, 2006 by American Chemical Society.

J.J. Davis et al., A SWNT Glucose Biosensor, Chem Eur. J., 2003, vol. 9, pp. 3732-3739, Wiley-VCH Verlag GmbH & Co., Weinheim.

Z. Lu et al., Dendrimer-Mediated Synthesis of Water-Dispersible Carbon-Nanotube-Supported Oxide Nanoparticles, J. Phys. Chem., 2007, vol. 111, pp. 8459-8462, published on Web May 27, 2007 by American Chemical Society.

B. Pan et al., Growth of multi-amine terminated poly(amidoamine) dendrimers on the surface of carbon nanotubes, Nanotechnology, 2006, vol. 17, pp. 2482-2489, IOP Publishing Ltd, published May 24, 2006, UK.

M. Sano, et al., Construction of Carbon Nanotube "Stars" with Dendrimers, Communications, Angew. Chem. Int. Ed. 2001, vol. 40, No. 24, pp. 4661-4663, Wiley-VCH Verlag GmbH, Weinheim, 2001.

L. Tao, et al., Modification of multi-wall carbon nanotube surfaces with poly(amidoamine) dendrons: Synthesis and metal templating, Communication, Chem. Commun., 2006, pp. 4949-4951, published on Web Oct. 9, 2006, UK.

Y. Yang, et al., Multiwalled Carbon Nanotubes Functionalized by Hyperbranched Poly(urea-urethane)s by a One-Pot Polycondensation, Macromolecular Rapid Communications, 2006, vol. 27, pp. 1695-1701, Wiley-VCH Verlag GmbH, Weinheim.

YL Zeng, et al., Functionalization of multi-walled carbon nanotubes with poly(amidoamine dendrimer for mediator-free glucose biosensor, Electrochemistry Communications, 2007, vol. 9, pp. 185-190, Elsevier B.V., published on web Oct. 5, 2006.

G. Ionova, et al., Mechanism f trivalent actinide/lanthanide separation using synergistic mixtures of di(chlorophenyl)dithiophosphinic acid and neutral O-bearing co-extractants, New J. Chem., 2001, vol. 25, pp. 491-501, published on Web Feb. 16, 2001, France.

G. Modolo, et al., Diamex Counter-Current Extraction Process for Recovery of Trivalent Actinides from Simulated High Active Concentrate, Separation Science and Technology, vol. 42, No. 3, Feb. 2007, pp. 439-452, Taylor and Francis Ltd.

H. Dam, et al., Multicoordinate ligands for actinide/lanthanide separations, Chem. Soc. Rev., 2007, vol. 36, pp. 367-377, published on Web Oct. 12, 2006.

B. Gruner et al., Cobalt bis(dicarbollide) ions with covalently bonded CMPO groups as selective extraction agents for lanthanide and actinide cations from highly acidic nuclear waste solutions, New J. Chem., 2002, vol. 26, pp. 1519-1527, published on Web Sep. 5, 2002, France.

L. Mikulasek, et al., Synergistic effect of ligating and ionic functions, prearranged on a calyx[4]arene, Chem. Commun., 2006, pp. 4001-4003, published on Web Aug. 14, 2006, UK.

M.M. Reinoso-Garcia, et al., CMP(O) tripodands : synthesis, potentiometric studies and extractions, New J. Chem., 2006, vol. 30, pp. 1480-1492, published on Web Mar. 21, 2006, France.

L.H. Delmau, et al., CMPO-Substituted' calix[4]arenes, extractants with selectivity among trivalent lanthanides and between trivalent actinides and lanthanides, Chem. Commun., 1998, pp. 1627-1628, UK.

M.G. Gorbunova, et al., New amino-functionalized 1,3-alternate calyx[4]arene bis- and mono-(benzo-crown-6 ethers) for pH-switched cesium nitrate extraction, Tetrahedron Letters, 2003, vol. 44, pp. 5397-5401, Elsevier Science Ltd.

S. Campidelli et al., Dendrimer-Functionalized . . . , J. Am. Chem. Soc., 2006, vol. 128, pp. 12544-12552, published on Web Sep. 6, 2006 by American Chemical Society.

SH Hwang et al., Dendron-Tethered . . . , J. Am. Chem. Soc., 2006, vol. 128, pp. 7505-7509, published on Web May 23, 2006 by American Chemical Society.

Z. Lu et al., Dendrimer-Mediated . . . , J. Phys. Chem., 2007, vol. 111, pp. 8459-8462, published on Web May 27, 2007 by American Chemical Society.

B. Pan et al., Growth of multi-amine . . . , Nanotechnology, 2006, vol. 17, pp. 2483-2489, IOP Publishing Ltd, published May 24, 2006, UK.

M. Sano, et al., Construction of Carbon . . . , Communications, Angew. Chem. Int. Ed. 2001, vol. 40, No. 24, pp. 4661-4663, Wiley-VCH Verlag GmbH, Weinheim, 2001.

L. Tao, et al., Modification of multi-wall . . . , Communication, Chem. Commun., 2006, pp. 4949-4951, published on Web Oct. 9, 2006, UK.

Y. Yang, et al., Multiwalled Carbon . . . , Macromolecular Rapid Communications, 2006, vol. 27, pp. 1695-1701, Wiley-VCH Verlag GmbH, Weinheim.

YL Zeng, et al., Functionalization of multi-walled . . . , Electrochemistry Communications, 2007, vol. 9, pp. 185-190, Elsevier B.V., published on web Oct. 5, 2006.

G. Ionova, et al., Mechanism of . . . , New J. Chem., 2001, vol. 25, pp. 491-501, published on Web Feb. 16, 2001, France.

G. Modolo, et al., Diamex Counter-Current . . . , Separation Science and Technology, vol. 42, No. 3, Feb. 2007, pp. 439-452, Taylor and Francis Ltd.

B. Gruner et al., Cobalt bis(dicarbollide) . . . , New J. Chem., 2002, vol. 26, pp. 1519-1527, published on Web Sep. 5, 2002, France.

L. Mikulasek, et al., Synergistic effect of ligating . . . , Chem. Commun., 2006, pp. 4001-4003, published on Web Aug. 14, 2006, UK.

M.M. Reinoso-Garcia, et al., CMP(O) tripodands : synthesis, . . . , New J. Chem., 2006, vol. 30, pp. 1480-1492, published on Web Mar. 21, 2006, France.

L.H. Delmau, et al., CMPO-Substituted' calix[4]arenes, extractants with . . . , Chem. Commun., 1998, pp. 1627-1628, UK.

M.G. Gorbunova, et al., New amino-functionalized 1,3-alternate . . . , Tetrahedron Letters, 2003, vol. 44, pp. 5397-5401, Elsevier Science Ltd.

* cited by examiner

FUNCTIONALIZED CARBON NANOTUBES, RECOVERY OF RADIONUCLIDES AND SEPARATION OF ACTINIDES AND LANTHANIDES

CROSS-REFERENCE

This application claims the priority filing date of U.S. Provisional Application Ser. Nos. 60/998,005 filed Oct. 9, 2007 and 60/998,872 filed Oct. 12, 2007, herein fully incorporated by reference.

FIELD OF THE INVENTION

Methods and compositions to extract radionuclides such as various actinides and lanthanides from organic and/or aqueous solutions by utilizing extractant functionalized carbon nanotubes are disclosed. More particularly, phosphorous-containing (such as phosphine oxides, phosphoric acids or phosphates) organic extractants and other predesigned extractants (such as crown ethers, calixcrown derivatives, malonamide and diglycolamide derivatives, polyethylene glycol derivatives, cobalt dicarbollide derivatives, and N-donating heterocyclic ligands) can be covalently and/or non-covalently employed on the surfaces and/or ends (tips) of carbon nanotubes for the purpose of removal radionuclides such as various actinides and lanthanides from organic and/or aqueous solutions. Extractant functionalized carbon nanotubes can be used for extracting radioactive nuclides from nuclear waste or spent nuclear fuel, which are produced and/or reprocessed from the nuclear power generation or other nuclear application. The invention also relates to the solid-liquid separation process based on the contact of liquid radioactive waste by using the invention extracting agents as the solid phase.

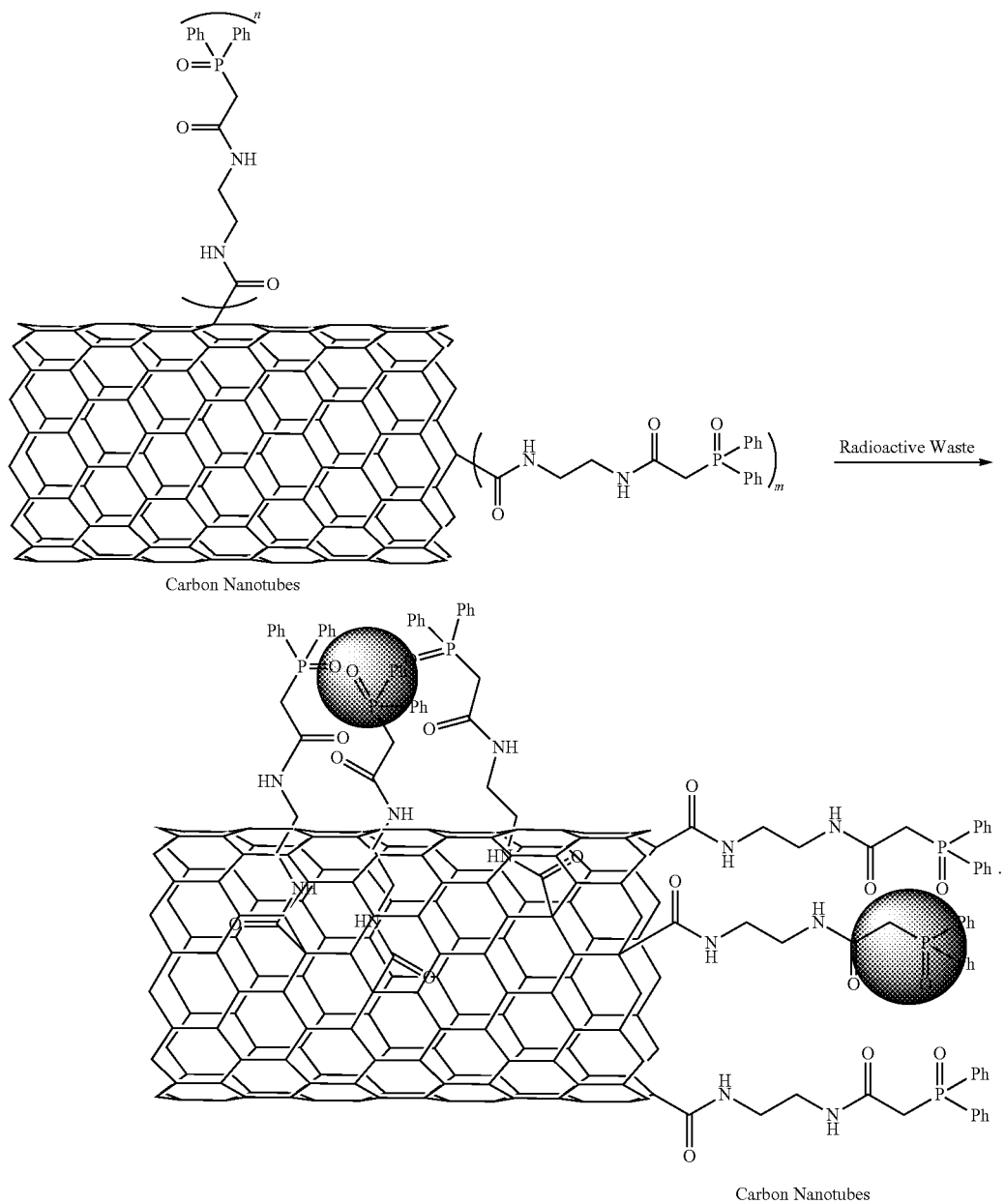

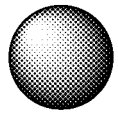 = Radionuclides

BACKGROUND OF THE INVENTION

Uranium is the most valuable energy material, 1 kg of uranium can generate ca. 500,000 megajoule of heat value comparison the same amount of coal only produces ca. 25 megajoules of heat value. Currently, developed and developing countries greatly rely on the nuclear power plants for electricity supply. In the United States, the nuclear energy plants supply ca. 20% of electricity. With the increasing fear to globe warming and shortage of foreign fuel, the solutions in energy security and energy independence are to expand the nuclear fission utilization and develop sustainable energy.

The harmful by-products derived from nuclear power plants during the electricity generation are radionuclides, including transuranic elements (TRU) with extremely long-lived isotopes, radioactive cesium and strontium, actinides, rare earth elements and lanthanides. Certainly, the hazardous materials in the radioactive liquid wastes need be reprocessed before depository in order to meet the government's requirement for diminishing the waste volume with the intention to avoid the second construction of repository. There is no current massive reprocessing activity in the United States, and most of spent nuclear wastes are stored in pools or nearby the reactor sites, for example, the Hanford Nuclear Reservation accumulates around 53 million gallons of nuclear waste. However, the nuclear wastes produced in foreign countries have been specifically treated to removal the hazardous radionuclides by using PUREX process or UNEX process. The largest reprocessing factory in the world is La Hague site located in France where annually ca. 1700 tonnes of nuclear spent fuel has been reprocessed; the rest of reprocessing plants are located in the United Kingdom, Japan, Russia and China.

Radioactive liquid wastes, including high level, intermediate level and low level wastes, can be categorized as two kinds of high level waste, namely fission products and transuranics, which must be managed to remove the harmful radioisotope nuclides before disposal or reuse.

Some of these high-level radioactive aqueous solutions have to be geologically disposed in long term storage (for example Yucca Mountain) due to the long lived elements, such as actinides, lanthanides, $^{90}$Sr and $^{137}$Cs. Management of long-lived radionuclides-containing wastes has offered advantages to develop unique separation technologies to meet the government policy requirement. Apparently, in order to minimize the capacity of waste, the imperative task is to develop extractant or ligand capable of extracting radioactive elements from acidic or high salinity solution in high selectivity and efficiency.

The TRUEX liquid-liquid extraction has been applied for the recovery of lanthanides and actinides from nuclear waste by utilizing the organophosphorous ligand, octyl-phenyl-N,N-diisobutyl-carbamoylmethyl-phosphine oxide (U.S. Pat. No. 4,548,790/1985).

The PUREX process is used to extract plutonium and uranium from the reprocessing spent nuclear fuel and from one another by liquid-liquid extraction. The active organic extractant (30% tributyl phosphate dissolving in kerosene, see U.S. Pat. No. 4,574,072/1986) transfers the plutonium and uranium from aqueous acidic spent nuclear fuel to organic phase.

Also alkyl-functional phosphoric acid derivatives can complex actinides and lanthanides (Ionova et al., *New J. Chem.*, 2001, 25, 491-501).

Ligands contain only CHNO (carbon, hydrogen, nitrogen and oxygen) elements give the opportunities to avoid the additional pollution during the burn-up process. Currently, DIAMEX process (*Sep. Sci. Techol.*, 2007, 42, 439-452) uses N,N'-dimethyl-N,N'-dibutyl-tetradecylmalonamide as extractant for separating actinides and lanthanides from nuclear waste by a solvation process. Besides the advantage of without the secondary waste, malonamide derivatives have confirmed their excellent complex efficiencies.

Crown Ether and polyethylene glycol derivatives have been applied to remove some radioisotopes, particularly Sr, Cs and small amount of actinides which are remaining during the reprocessing of used spent nuclear fuel.

As mentioned above, removal of radioactive cesium and strontium, as well as minor actinides is particularly vital in the reprocessing of nuclear waste raffinates. More than two decades ago, scientists have started to exploit the ionic halogenated derivatives of cobalt dicarbollide possessing excellent capability to extract $^{137}$Cs as the extractant to extract the acidic waste raffinates, and subsequently realize the importance when combining with polyethylene glycol (PEG), since the complex extractant system of (COSAN-PEG) or (CCD-PEG) can be used for synergistically extracting strontium.

A recent industrial liquid-liquid extraction process has been developed in Russia by using the combining extractant system (CCD-PEG), called "UNEX", to remove the radioactive waste of Cs, Sr and minor actinides. The organic solvents used in "UNEX" are nitrobenzene or chloro-hydrocarbons.

U.S. Pat. No. 6,270,737 (Law et al from Idaho Engineering and Environmental Laboratory) disclosed the method to removal hazardous materials, such as radioactive Cs and Sr, by using non-aromatic solvent and the safe stripping agents. The method involved a synergistic extraction system comprising organoboron (for example chlorinated cobalt dicarbollide) and polyethylene glycol, the diluent solvents are the mixture of bis(tetrafluoropropyl ether of diethylene glycol) with bis(tetrafluoropropyl ether of ethylene glycol) et al.

The European Atomic Commission has recently launched a multinational project for the treatment of spent nuclear waste, called "EUROPART". "EUROPART" has devoted many contributions to the nuclear waste treatment technologies, for example Calix-CMPO (CMPO referred as carbamoylmethylphosphine oxides, Calix referred as calixarenes) and Calix-Crown. Interestedly, several groups from Europe have demonstrated the ideas by introducing cobalt dicarbollide (COSAN) derivatives to the frame of macrocyclic calxarenes (Mikulasek et al. *Chem. Commun.,* 2006, 4001-4003), as well as incorporate the COSAN and CMPO on the same molecules (Dam et al., *Chem. Soc. Rev.* 2007, 36, 367-377; Gruner et al. *New J. Chem.,* 2002, 26, 1519-1527; Reinoso-Garcia et al. *New J. Chem.,* 2006, 30, 1480-1492) for the treatment of nuclear waste. Unfortunately, all of those developments are still under the usage of organic solvent (such as nitrobenzene and dichloroethane et al) for the liquid-liquid extractions.

A ready to scale-up achievement including the using chlorinated cobalt dicarbollide (CCD) derivatives and polyethylene glycol (PEG) as one of the series of flowsheets has been developed at Argonne National Laboratory, called "UREX+" process. The advantage of this method is run sequentially in the same shielded-cell contactor and gloveboxes with segments of 1) CCD-PEG (removing Cs and Sr), 2) NPEX (removing Pu and Np), 3) TRUEX (removing Am, Cm, and rare earth), and 4) Cyanex-301 (separating Am and Cm from the heavy rare earths). In the stage of CCD-PEG, the organic solvent for solubilizing CCD-PEG is phenyltrifluoromethyl sulfone.

Calix[4]arene based extractants which attach carbamoylmethylphosphine oxide (hereafter, referred as CMPO) groups on their wide or narrow rims leads to more than two orders efficiency increase compared to octyl-phenyl-N,N-diisobutyl-carbamoylmethyl-phosphine oxide, also increase the selectivity to actinides and lanthanides (Delmau et al., *Chem. Commun.* 1998, 1627-1628).

US Patent Application No. 2001/6312653 B1 discloses a functionalized calixarenes with CMPO in the wide rim for using in the extraction of actinides and lanthanides. A phosphinoxidoacetamide moieties attached to the frame of the macrocyclic calixarene, this discovery is effective to remove actinides and lanthanides from the radioactive aqueous waste by liquid-liquid extraction.

US Patent Application No. 2006/0205920 A1 discloses a method to introduce CMPO groups to the terminal amino of dendrimers, such as PAMAM for extracting lanthanides and actinides. Those dendrimers ($2^{nd}$, $3^{rd}$, $4^{th}$ and $5^{th}$ generations) usually have multiple terminal amino groups which are readily functionalized by amide reaction for the purpose of introduction of CMPO substituents.

US Patent Application No. 2005/6843921 B1 discloses a method, which use the silica absorbent containing organophosphorus, such as octyl(phenyl)-N,N-diisobutylcarbamoylmethylphosphine oxide on the complex-carrier, for separating and recovering the radioactive liquid wastes. By the elution steps, the absorptive elements on the porous silica carrier particles are eluted separately.

US Patent No. 2001/6258333 B1 discloses an extracting method comprising an extracting agent composition for the treatment of nuclear waste which containing radioactive elements and rare earths by two phases liquid-liquid extractions. By utilizing an organoboron complex, organophosphorus and polyethylene glycol compounds, the selective sequential extraction processes were used for the recovery of radionuclides, also including rare earths and actinides.

US Patent No. 1995/5468456 discloses the using of magnetic particles which contacted the metals-containing liquids to concentrate the metals to the surface of the magnetic particles.

Other specifically designed ligands, for instance polyethylene glycol and crown ether functionalized calixarenes, namely calixcrowns, have developed (Gorbunova et al., *Tetrahedron Lett.* 2003, 44 (29), 5397-5401, WO94/24138) for approaching the separation of cesium, strontium and actinides.

SANEX process has been created for removal lanthanides to avoid poisoning a neutron driven nuclear reaction. French CEA is studying the extraction efficiency of using N-donating extractants, such as triazine-pyridine derivatives; one of the purpose is to extract Americium (Dam et al., *Chem. Soc. Rev.* 2007, 36, 367-377).

Carbon nanotubes (hereafter, referred as CNT) have high surface area, high electrical conductivity, high thermal conductivity and high mechanical strength. Owing to its exceptional chemical/physical stability, CNT has been used in harsh/corrosive environments, in particularly; CNT possesses extremely high resistance to acidic environment, for example $HNO_3$ aqueous solution, which allows to be used for the recovery of spent nuclear fuel.

The solubility of CNT can be improved by covalent and/or non-covalent modification. Harsh acid oxidative treatment of CNT by $H_2SO_4/HNO_3$ mixture produces oxidative function, also short residue of CNT (<200 nm length).

SUMMARY OF THE INVENTION

An object of the invention is to provide exceptionally stable and easy synthesized materials for extracting radionuclides such as various actinides and lanthanides by using organic and/or organoboron extractant functionalized carbon nanotubes. Carbon nanotubes are commercially available and have many advantageous properties due to their high surface area, high electrical conductivity, high mechanical strength and excellent chemical/physical stability that allow their use in harsh/corrosive environments. Up to now, no literature or patents were found disclosing various functionalized extractants such as a phosphorous containing derivative, a N-donating heterocyclic derivative, a malonamide derivative, a diglycolamide derivative, a crown ether derivative, a calixcrown derivative; a polyethylene glycol derivative, or a cobalt dicarbollide derivative connected to (chemically reacted with) carbon nanotubes as solid extractants in the application of treatment of nuclear waste, as well as separation of radionuclides such as various actinides and lanthanides.

The invention relates to chemically functionalized carbon nanotubes containing various functionalized extractants for extracting various radionuclides. An example of an extractant is a phosphorus-containing ligand, such as acetamidophosphine oxide (CMPO), utilizes commercial available or modified CNT possessing terminal carboxylic acid (COOH), amino ($NH_2$), hydroxy (OH) and/or thio (SH) groups as the active sites for the purpose of introducing phosphorus-containing reactants. The acetamidophosphine oxide (CMPO) functionalized CNT has following formula (I):

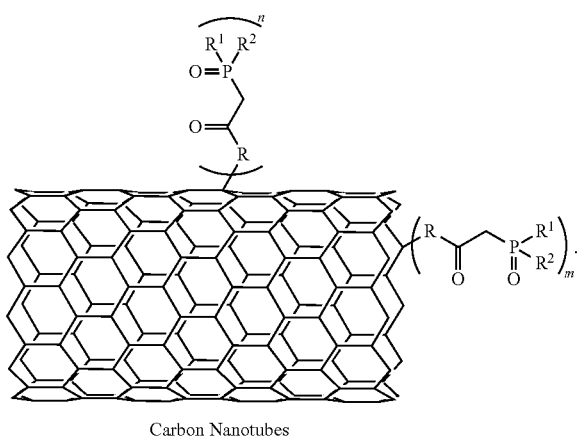

Formula I

Carbon Nanotubes wherein each R of the "n" and "m" groups, independently, is the CNT and CMPO connecting groups, includes dendritic molecules (dendrimers), hyperbranched molecules, polymers, amides, an alkyl having from 1 to about 20 carbon atoms, an aryl group including an aliphatic or an alkyl substituted aryl wherein the aliphatic or alkyl group has from 1 to about 20 carbon atoms, or a polyethylene glycol containing from 2 to about 100 repeat units, or combinations thereof. These groups can be linear or branched and desirably have from 1 to about 10 carbon atoms. Those connecting groups must have at least one terminal active group, for example amine ($NH_2$), in order to covalently connect organophosphorous moieties on CNT. Other connecting groups for Formula I as well as all other formula in this specification include hydroxyl, halogen, and carboxylic acid.

Each $R^1$ and $R^2$ of the "n" and "m" groups, independently, include various groups such as aryl as well as aliphatic or alkyl substituted aryl groups wherein the aliphatic and the alkyl group contain from 1 to about 20 carbon atoms, or an aliphatic or an alkyl group having from 1 to about 20 carbon atoms. The $R^1$ and $R^2$ groups can be alkoxy groups having from 1 to about 20 carbon atoms such as methoxy and ethoxy. These groups can be linear or branched and preferably have from 1 to about 10 carbon atoms.

The n and m stand for the number of functional groups of either the end functionalized extractant group or the surface functionalized extractant group, i.e. the surfaces or ends (or tips) of the CNT. This number is generally unknown and will depend upon various factors such as the diameter of each nanotube, the length of each nanotube, and the number of inherent functional groups that reside on a nanotube such as carboxylic acid group, an amino group, a hydroxy group, and the like. For example n and m, independently, can possibly range from about 0.01 atom % to about 30 atom % of total carbon atoms of CNT, preferably having from 0.1 atom % to 10 atom %, and the like. This statement is true with regard to all of the formulas set forth in this specification, that is, Formulas I through IX, IA, IIA, IIIA, and VIA.

Physically wrapping CNT with CMPO compounds can provide a non-covalent method to produce the solid extractants for the same purpose of extracting radionuclides, actinides and lanthanides from nuclear waste.

Various other functionalized radionuclides extractants attached to carbon nanotubes are set forth below in Formulas II through VI, IA, IIA, IIIA, VIA, VIII, and IX.

The following formula (II) illustrates a method for preparation of CMPO analogues functionalized CNT.

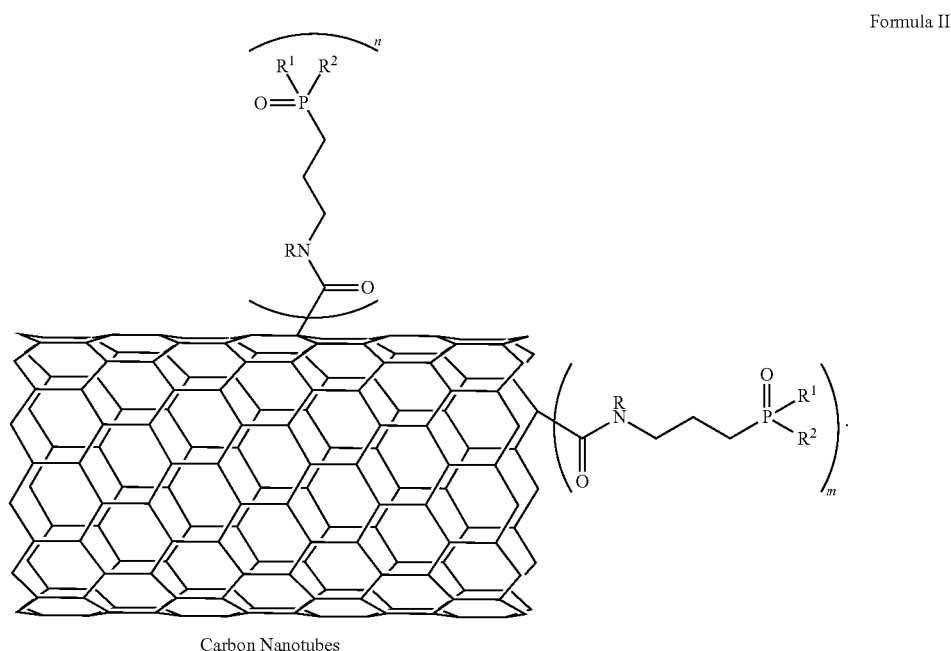

Formula II

Carbon Nanotubes

Each R of the "n" and "m" groups, independently, is hydrogen, an aliphatic or an alkyl having from 1 to about 20 carbon atoms, an aryl or a substituted aliphatic aryl or an alkyl substituted aryl wherein the aliphatic or alkyl group has from 1 to about 20 carbon atoms, or a polyethylene glycol having from about 2 to about 100 repeat units. These groups can be linear or branched, and desirably have from 1 to about 10 carbon atoms. The alkyl groups between the phosphine oxide and amide can also be linear or branched and have from 1 to about 20 carbon atoms, such as methyl, ethyl, n-propyl, i-propyl, n-butyl and i-butyl groups.

Each $R^1$ and $R^2$ of the "n" and "m" groups, independently, can be an aryl or an aliphatic substituted or an alkyl substituted aryl with the aliphatic or alkyl group containing from 1 to about 20 carbon atoms, an alkoxy having from 1 to about 20 carbon atoms such as methoxy or ethoxy, an aliphatic or an alkyl having from 1 to about 20 carbon atoms, and the like. These groups can be linear or branched. Generally, 1 to 10 carbon atoms are preferred.

Physically wrapping CNT with CMPO-liked functional compounds can supply a non-covalent method to produce the solid extractants for the same purpose of extracting radionuclides, actinides and lanthanides from nuclear waste.

The following formula (III) illustrates a method for attaching functionalized organophosphates on CNT.

Formula III

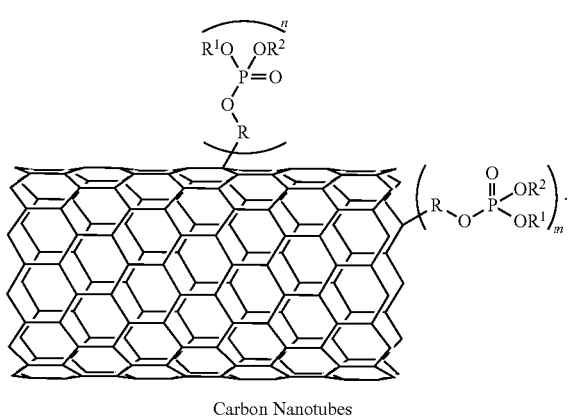

Carbon Nanotubes

Each R of the "n" and "m" groups, independently, is the CNT and organophosphate connecting group, such as dendritic molecules (dendrimers), hyperbranched molecules, polymers, amides, an aliphatic such as an alkyl having from 1 to about 20 carbon atoms, an aryl or an aliphatic substituted aryl or an alkyl substituted aryl wherein the aliphatic and the alkyl contains from 1 to about 20 carbon atoms, or a polyethylene glycol containing from 2 to about 100 repeat units, as well as combinations thereof. These groups can be linear or branched and desirably have from 1 to about 10 carbon atoms. These connecting groups must have at least one terminal active group, for example hydroxy (OH), in order to covalently connect organophosphate moieties on CNT.

$R^1$ and $R^2$ independently, can be an aryl or an aliphatic substituted aryl or an alkyl substituted aryl wherein the aliphatic and the alkyl group has from about 1 to about 20 carbon atoms, or an aliphatic or an alkyl having from 1 to about 20 carbon atoms, and the like. These groups can be linear or branched. Generally, 1 to 10 carbon atoms are preferred.

Physically wrapping CNT with phosphate functional compounds can supply a non-covalent method to produce the solid extractants for the same purpose of extracting radionuclides, actinides and lanthanides from nuclear waste.

Following formula (IV) illustrates the combination of phosphoric acids and CNT:

Formula IV

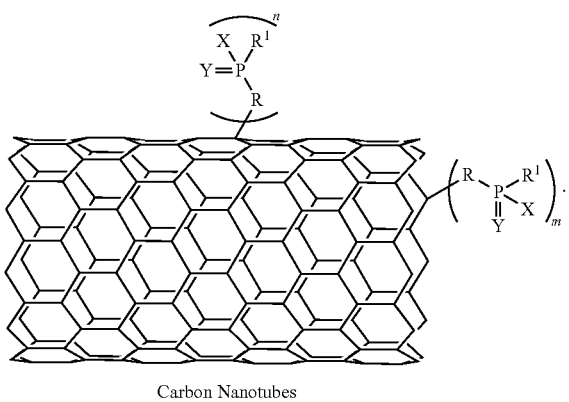

Carbon Nanotubes

Each R of the "n" and "m" groups, independently, is the CNT and phosphoric acid connecting group, such as dendritic molecules (dendrimers), hyperbranched molecules, polymers, amides, an aliphatic or an alkyl having from 1 to about 20 carbon atoms, an aryl or an aliphatic substituted aryl or an alkyl substituted aryl wherein the aliphatic and the alkyl group contain from 1 to about 20 carbon atoms, or a polyethylene glycol containing from 2 to about 100 repeat units, as well as combinations thereof. These groups can be linear or branched and desirably have from 1 to about 10 carbon atoms. These connecting groups must have at least one terminal active reaction groups, for example but not limited to hydroxy (OH) and/or halogen (I and/or Br), in order to introduce organophosphoric acids moieties on CNT.

$R^1$ of the "n" and "m" groups, independently, is an aryl or an aliphatic substituted or an alkyl substituted aryl wherein the aliphatic and the alkyl group contain from 1 to about 20 carbon atoms, an alkoxy containing from about 1 to about 20 carbon atoms such as methoxy or ethoxy, or an aliphatic such as an alkyl group containing from about 1 to about 20 carbon atoms. These groups can be linear or branched. Generally, 1 to about 10 carbon atoms are preferred. X is hydroxy (OH) or thio (SH); Y is oxygen (O) or sulfur (S).

Physically wrapping CNT with functional phosphoric acid derivatives may supply a non-covalent method to produce the solid extractants for the same purpose of extracting radionuclides, actinides and lanthanides from nuclear waste.

The following formulas show two predesigned materials related to the attachments of malonamide (formula V) or diglycolamide (formula VI) derivatives on CNT (only containing CHNO elements).

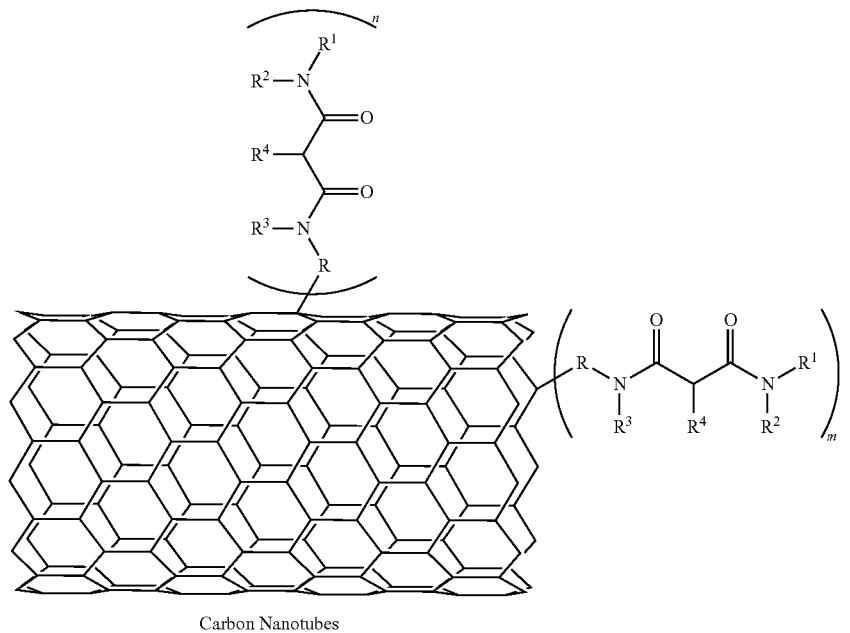

Formula V

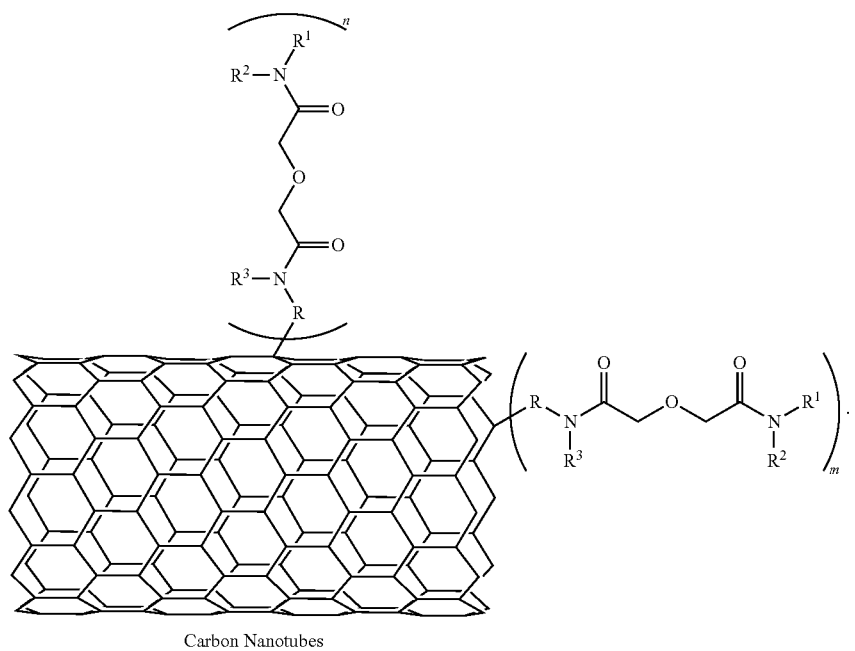

Formula VI

In both formula, each R of the "n" and "m" groups, independently, is the CNT-extractant connecting group, such as dendritic molecules (dendrimers), hyperbranched molecules, polymers, amides, an aliphatic or an alkyl having from 1 to about 20 carbon atoms, an aryl or an aliphatic substituted or an alkyl substituted aryl wherein the aliphatic or alkyl group contains from 1 to about 20 carbon atoms, or a polyethylene glycol containing from 2 to about 100 repeat units, as well as combinations thereof. These groups can be linear or branched and desirably have from 1 to about 10 carbon atoms. These connecting groups must have at least one terminal active reaction groups, for example but not limited to amine ($NH_2$), hydroxy (OH) or carboxylic acid (COOH), in order to introduce those organic extractants on CNT.

In both formulas, each $R^1$ and $R^2$ of the "n" and "m" groups, independently, can be an aryl or an aliphatic substituted or an alkyl substituted aryl wherein the aliphatic and the alkyl group has from about 1 to about 20 carbon atoms, or an aliphatic or an alkyl having from 1 to about 20 carbon atoms, and the like. These groups can be linear or branched. Generally 1 to 10 carbon atoms are preferred.

Each $R^3$ and $R^4$ of the "n" and "m" groups, independently, can be hydrogen, an aryl or an aliphatic or an alkyl substituted aryl wherein the aliphatic and the alkyl group has from 1 to about 20 carbon atoms, or an aliphatic or an alkyl having from 1 to about 20 carbon atoms. These groups can be linear or branched and generally 1 to about 10 carbon atoms are preferred.

Physically wrapping CNT with malonamide or diglycolamide functional compounds may supply a non-covalent method to produce the solid extractants for the same purpose of extracting radionuclides, actinides and lanthanides from nuclear waste.

The following formula relates to an extractant functionalized carbon nanotube containing dendritic crown ethers.

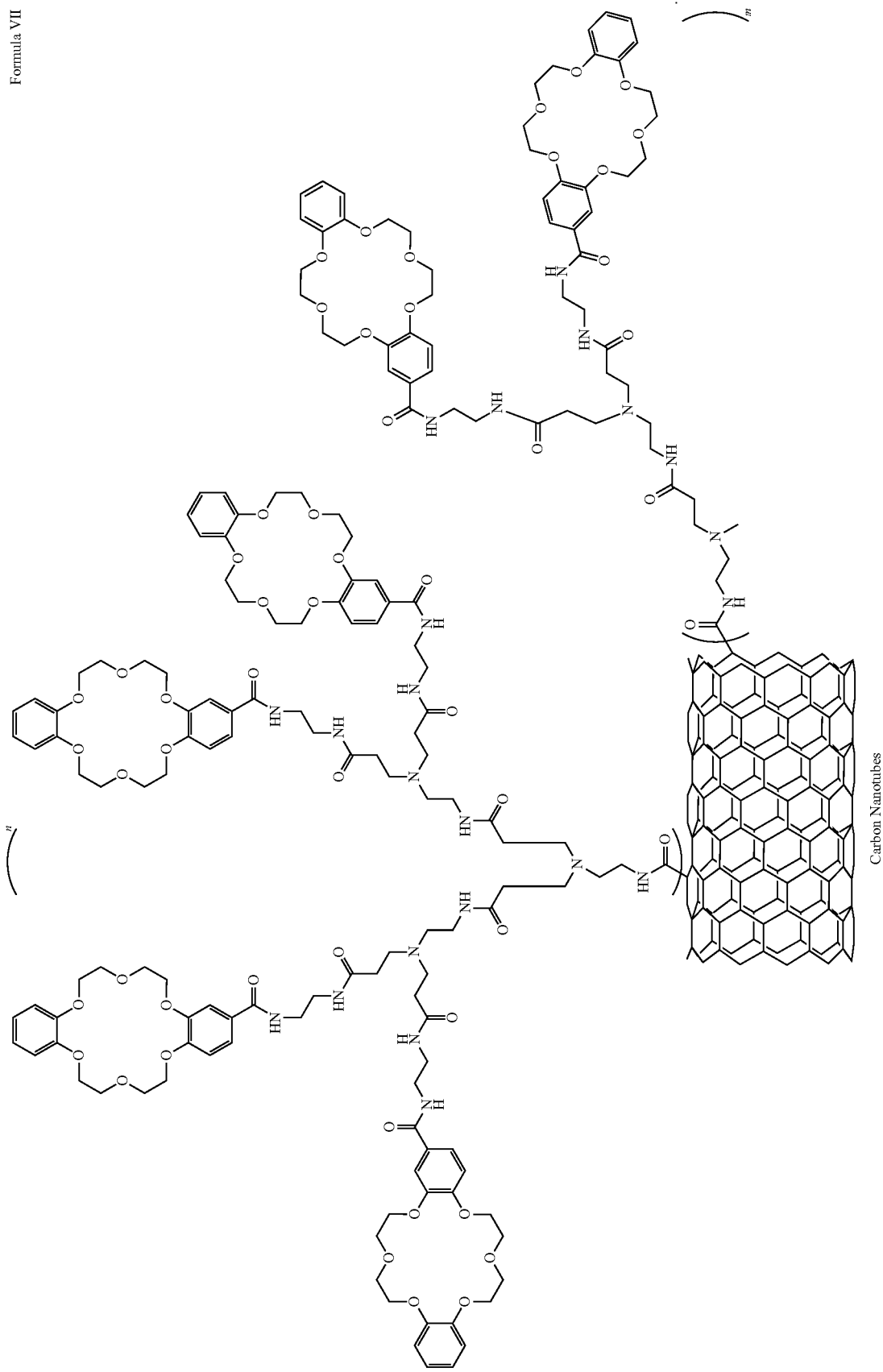

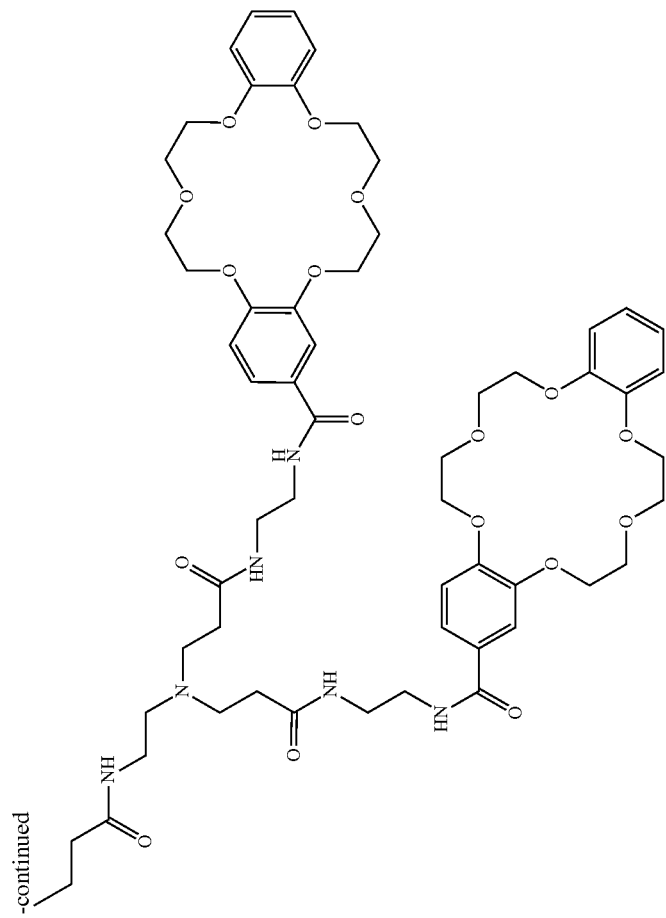

DETAILED DESCRIPTION OF THE INVENTION

Figure 1:
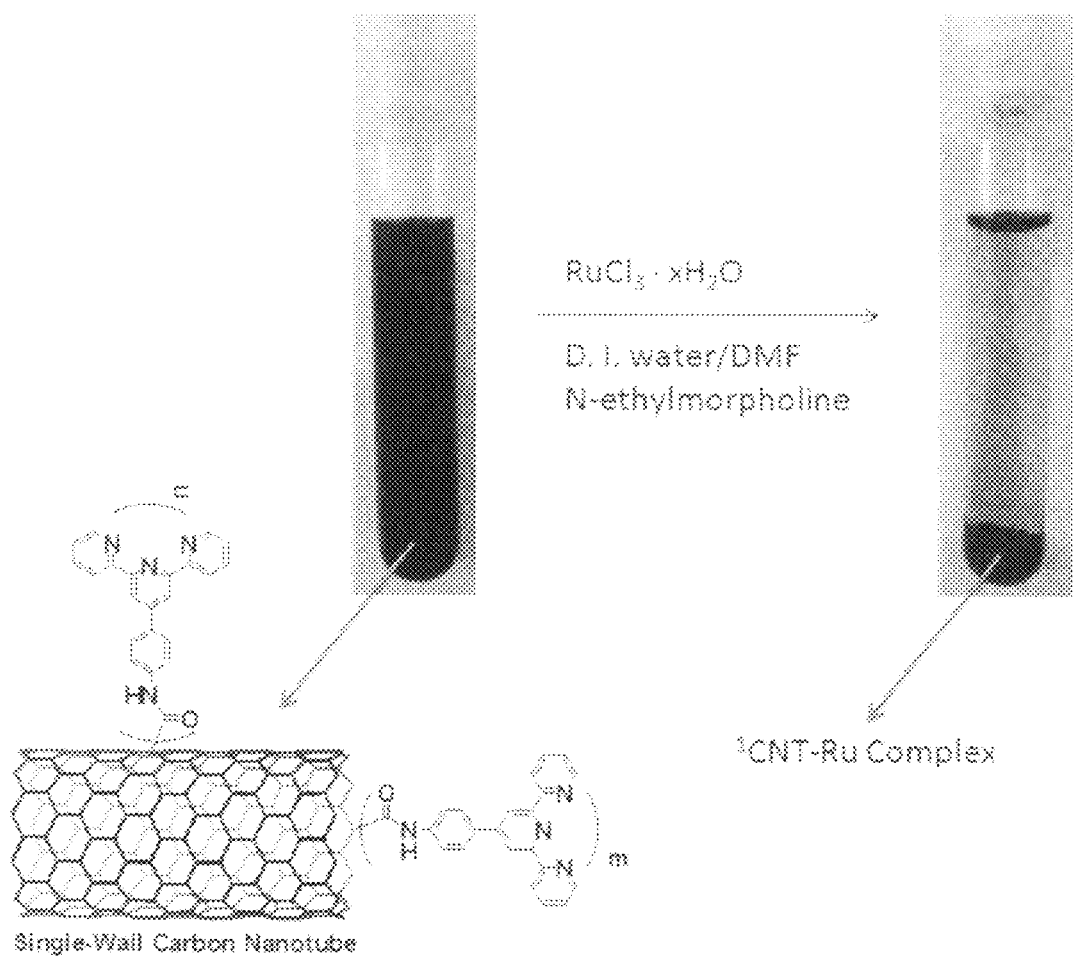
FIG. 1 is a representative photograph showing the terpyridine functionalized CNT (Tpy-CNT) reacting with $RuCl_3$.
Figure 2:
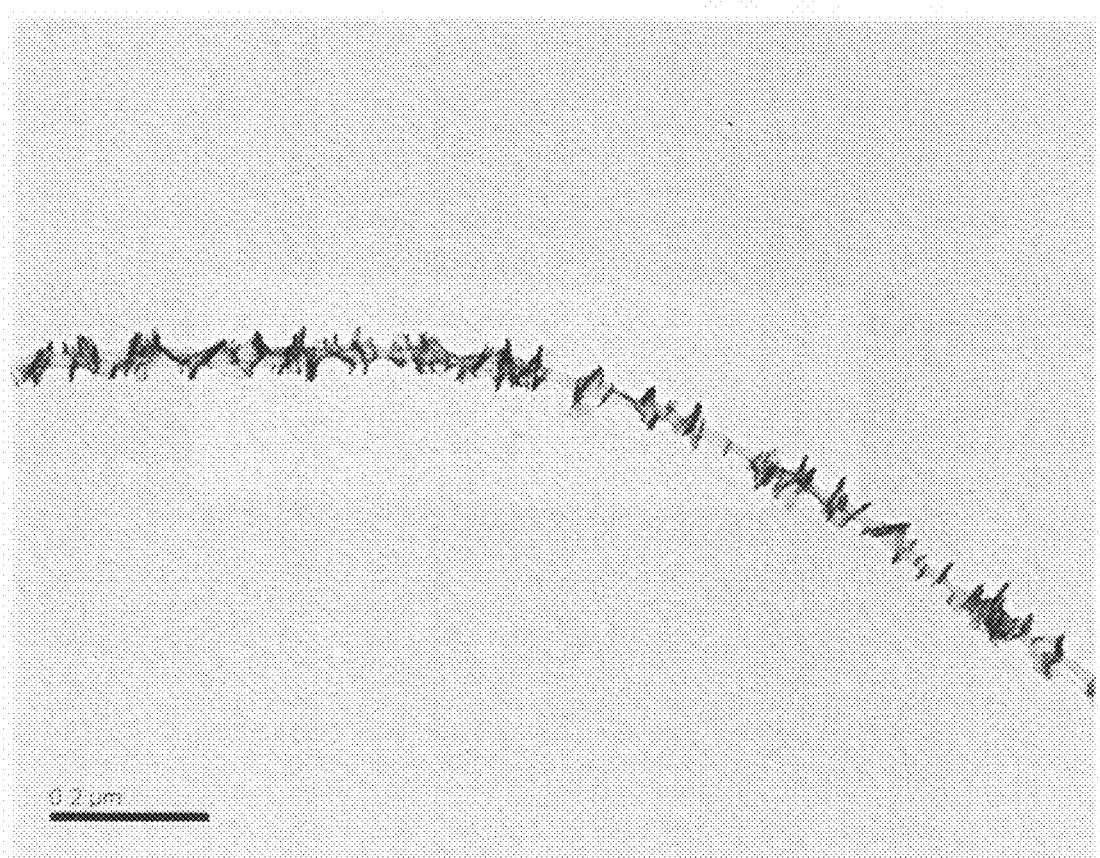
FIG. 2 is a transmission electron microscope image of the reaction product ($^1$CNT-Ru Complex) formed in FIG. 1. Scale bar: 0.2 μm.
Figure 3:
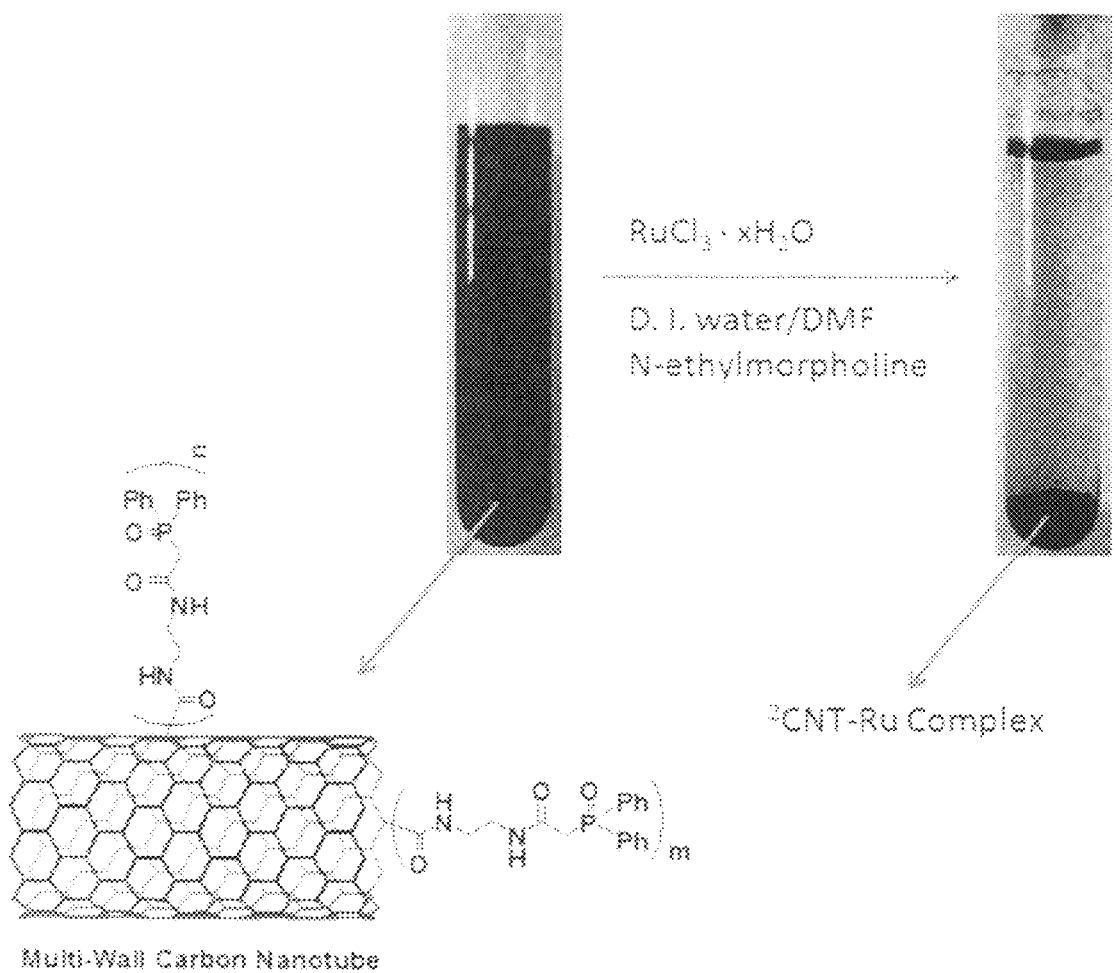
FIG. 3 is a representative photograph showing CMPO functionalized CNT (CMPO-CNT) reacting with $RuCl_3$.
Figure 4:
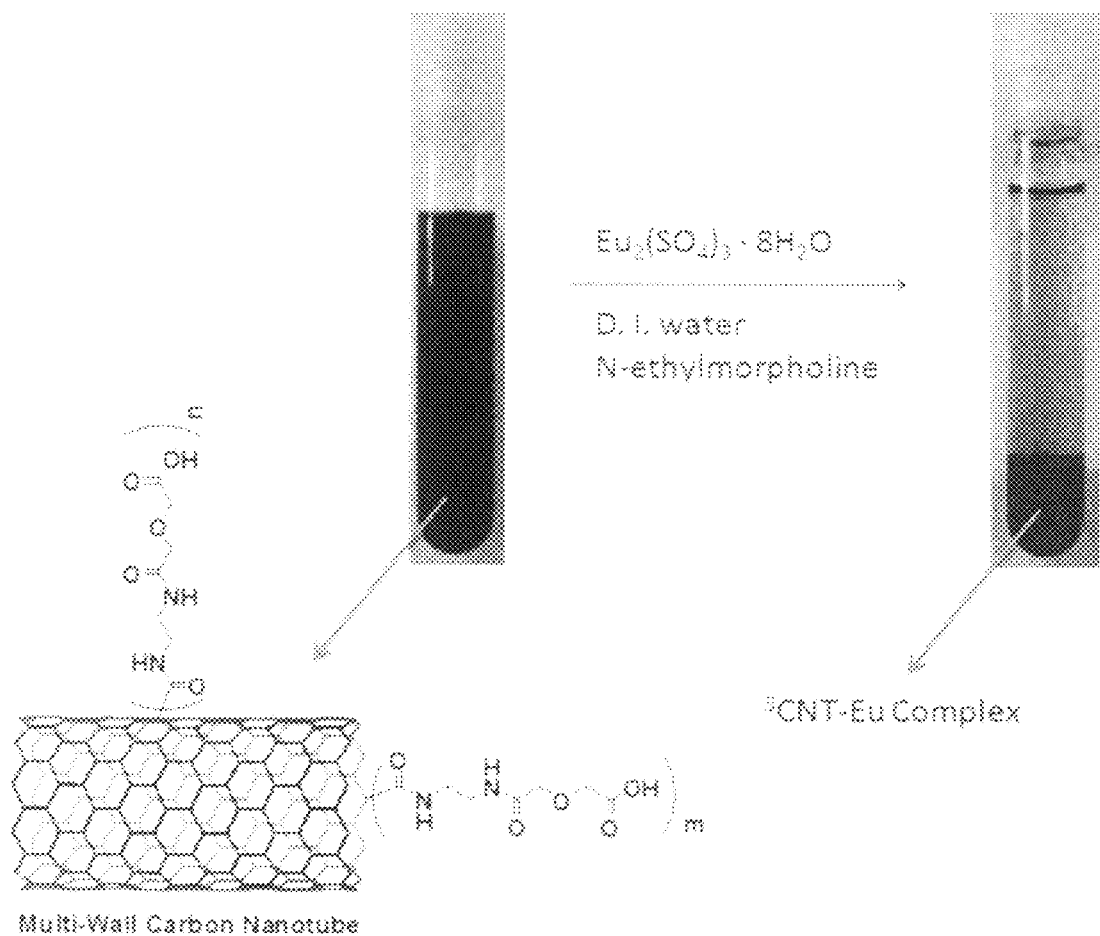
FIG. 4 is representative photograph showing diglycolamide functionalized CNT (DiglyAmide-CNT) reacting with $Eu_2(SO_4)_3$.

The carbon nanotubes (CNT) described in present invention have the following general formula, wherein the graphic drawing does not represent the exact forms of carbon nanotubes, but only for the purpose of simplification see (Dresselhaus et al., *Carbon Nanotubes: Synthesis, Structure, Properties, and Applications*; Springer: Berlin, 2001), hereby fully incorporated by reference.

Formula VIII

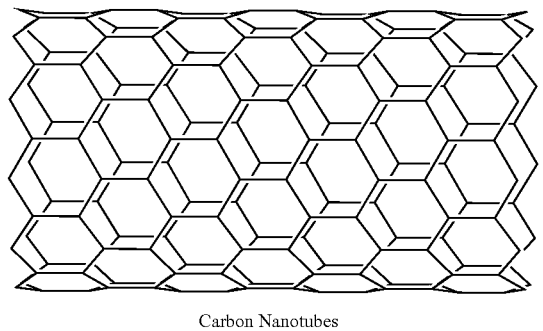

Carbon Nanotubes

One embodiment of the invention is the production of functionalized carbon nanotubes (CNT) containing various functional extractants, such as phosphorous-containing ligands, malonamide and/or diglycolamide derivatives, crown ether derivatives, calixcrown derivatives, amide derivatives, N-donating heterocyclic derivatives, polyethylene glycol derivatives, cobalt dicarbollide derivatives, or combinations thereof. The number of functionalized extractant compounds attached on CNT depends on the terminal groups that existed prior to attachment of the functionalized extractants compounds. The functionalized CNT of the invention may be used as extractants (as the solid phases) of actinides and lanthanides from solutions containing them, as well used in the field of reprocessing spent nuclear fuel. The method of extraction can comprise solid-liquid processes; or liquid phases are either aqueous and/or organic phases. The liquid phases include, but are not limited to radioactive nuclear waste, industrial waste, ore refinery and heavy metals containing water and/or organic solutions.

The carbon nanotubes (CNT) used in the present invention include a single-wall carbon nanotube, double-wall carbon nanotube, multi-wall carbon nanotube and carbon nanohorn. As prepared and commercially available, pristine CNT can be modified by, but not limited to acid oxidation at defects sites or ends (tips), plasma treatment, 1,3-dipolar cycloadditions, Diels-Alder cycloaddition, azo-radical reaction, photoinduced addition, π-π and/or σ-π interactions. These modified CNT have, according to the invention, terminal polycarboxylic acid (COOH), amine ($NH_2$), hydroxy (OH) and thio (SH) groups, that can be identical or different, i.e. any combination thereof. Actually, CNT itself is capable of acting as ligands to form complexes with actinides and lanthanides, particularly those having functional groups such as, but not limited to, polycarboxylic acids (—COOH), amino (—$NH_2$), amides (—CONH—), dendritic molecules (dendrimers), hyperbranched molecules and polymers. Thus, they can be the excellent candidates for the separation of actinides and lanthanides.

As available, pristine carbon nanotubes can be modified by oxidative acids treatments, such as carboxylic acids that can shorten the CNT length at their defects. Based on the structure of oxidized CNT, predesigned chemical attachments of organophosphorous can be realized through the utilization of carboxylic acids groups. For example, CMPO functionalized CNT (hereafter, referred as CMPO-CNT) illustrates in the Formula 1, carbonyl chloride of CNT can react with excess ethylenediamine to create terminal amino ($NH_2$) on CNT, wherein supplying the sites for the chemical introduction of CMPO groups.

CMPO-CNT is a solid with excellent stability in aqueous acidic environment. CMPO-CNT can be soluble or suspended either in organic or aqueous solutions. Therefore the invention has the advantages to be used in various environments, for example for the reprocessing spent fuel, CMPO-CNT and/or other CNT-extractant compositions can directly be added to the organic and/or aqueous acidic solutions to employ the solid-liquid extraction in place of liquid-liquid extractions (such as PUREX, UREX, TRUEX, DIAMEX, SANEX processes, that produce the secondary contaminated organic solution, for instance kerosene or $CH_2Cl_2$). Moreover the CMPO-CNT and/or other CNT-extractants compositions can be used for the treatment of radioactive liquid waste (such as intermediate level and low level wastes) that are produced after reprocessing, but still containing minor radioactive contents.

The solid-liquid extraction processes can be incorporated with/without catalytic amount of reduced reagents, such as, but not limited to, N-ethylmorpholine.

The solid-liquid extraction process can be accomplished by mixing CMPO-CNT and/or other extractive composition of the present invention with radioactive waste solution along with agitating, shaking, heating and sonication, combination operations thereof; finally the complex can be separated by, but not limited to, filtration, centrifuge, dialysis, or combinations thereof. The solid extractant compositions can be prepared as filter film, column chromatographic filling, or mixing with solid supports (such as $SiO_2$, $TiO_2$, $SnO_2$, $Al_2O_3$, $H_4SiW_{12}O_2$, celite and ceramic).

The functionalized CNT can be connected each other by a bifunctional and/or multifunctional organic extractant compounds (including, but not limited to diglycolyl chloride, bifunctional organophosphorous reactants, bifunctional crown ether and/or bifunctional glycol chain reactants) to provide a polymeric or hyperbranched CNT-extractant network that can assist to achieve higher extraction efficiency due to synergetic interaction, and also to facilitate the generation of thin-film due to their polymer-liked characters.

In one embodiment of the invention, the terminal amino ($NH_2$), carboxylic acid (COOH), hydroxy (OH) and/or thio (SH) groups on CNT backbone can have dendritic, hyperbranched or polymeric molecular structures, or combinations thereof. An example of second generation functionalized dendritic molecules with terminal amino ($NH_2$) on CNT has more active sites (—$NH_2$) for the intention of introduction of more extractants, such as, but not limited to CMPO or crown ethers. See (Sano et al., *Angew. Chem. Int. Ed.* 2001, 40(24), 4661. Tao et al., *Chem. Commun.*, 2006, 4949. Davis et al., *Chem. Eur. J.* 2003, 9, 3732-3739. Campidelli et al., *J. Am. Chem. Soc.* 2006, 128, 12544-12552. Yang et al., *Macromol. Rapid Commun.* 2006, 27, 1695-1701. Pan et al., *Nanotechnology* 2006, 17, 2483-2489. Lu et al. *J. Phys. Chem. C* 2007, 111, 8459-8462. Zeng et al., *Electrochemistry Communications* 2007, 9, 185-190. Hwang et al., *J. Am. Chem. Soc.* 2006, 128, 7505-7509), all hereby fully incorporated by reference.

An alternative embodiment is to wrap the functionalized CNT with organic and/or inorganic materials with non-covalent interaction or deposition. The wrapped organic and/or inorganic materials can contain suitable extractant compounds or can be complementarily functionalized with the appropriate extractants compounds.

Another embodiment involves is attaching different combinations of extractants on CNT, that may synergistically coordinate the radioactive metals with higher extraction efficiency and selectivity.

The invention thus provides new and simple methods to prepare the useful carbon nanotubes based materials for the application in, but not limited to, recovery of radionuclides reprocessing spent nuclear fuel, extracting actinides and lanthanides, removal hazardous materials from liquid or gas, ore refinery, wastewater purifications, sensors and detectors, neutron moderators, composites with other liquid and solid phases, and sustainable energy materials.

The following examples serve to illustrate methods and embodiments of the invention in detail but do not limit the apparent possibilities of variations and modifications without departing from the scope of the invention.

EXAMPLES

Diethylcarbamoylmethylphosphonate or CMPO functionalized CNTs:
Diethylcarbamoylmethylphosphonate or CMPO Functionalized Multi-Wall Carbon Nanotubes

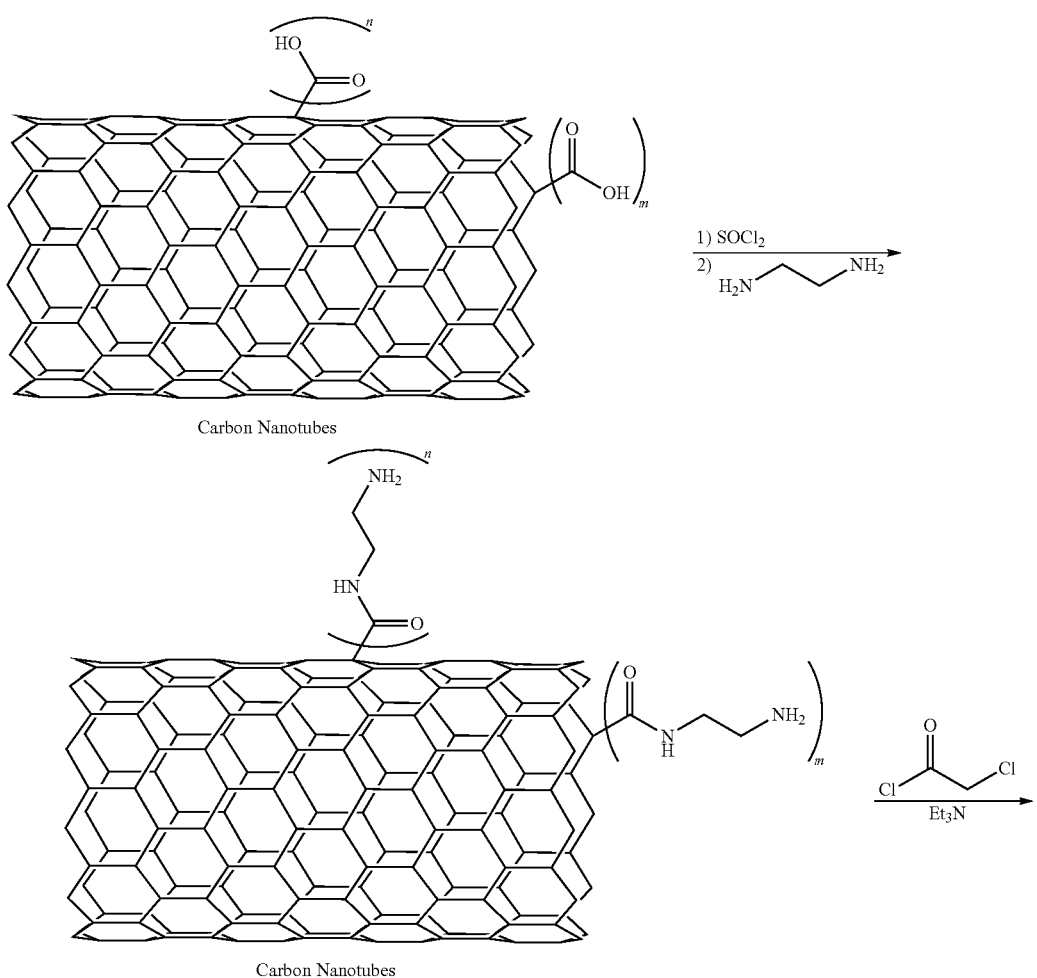

Formula I A

-continued

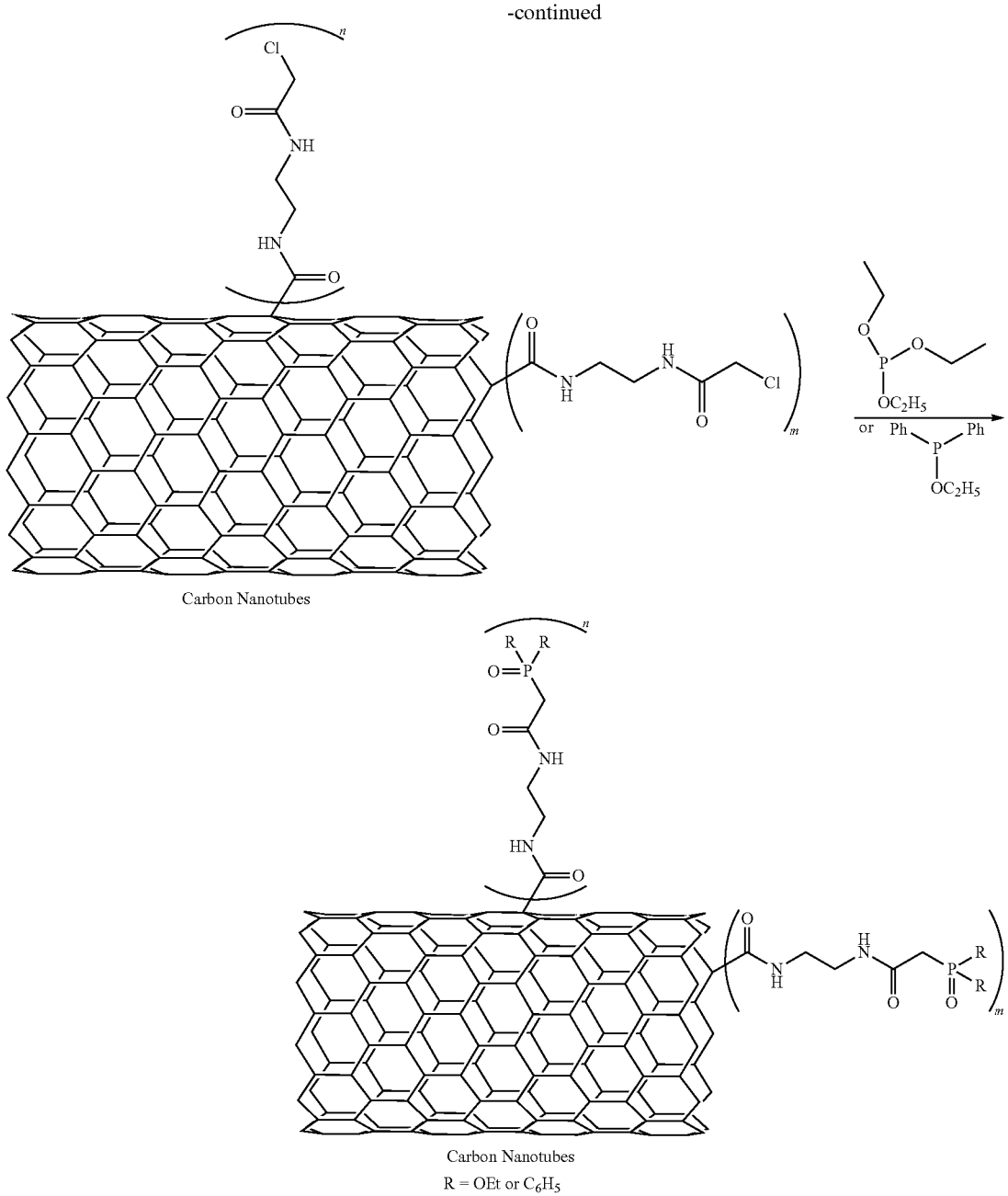

Carbon Nanotubes
R = OEt or $C_6H_5$ 1) 250 mg of carboxy-modified multi-wall carbon nanotube (MWNT-COOH) was sonicated with 30 ml of thionyl chloride for 30 minutes, and then stirred for 24 hours at room temperature to generate carbonyl chloride functional group (MWNT-COCl), that was directly used for next step without further purification.

2) MWNT-COCl in DMF was mixed with ethylenediamine (10.0 ml) and placed in an ultrasonic bath for 2 h at room temperature. The mixture was stirred for another 24 h at 90° C. The resulting solid was separated by vacuum filtration using 0.2 μm Millipore nylon membrane filter and repeatedly washed with acetone and methanol, respectively. The resulting solid was dried in a vacuum at room temperature, generating 255 mg of (MWNT-CONHCH$_2$CH$_2$NH$_2$).

3) 853 mg of (MWNT-CONHCH$_2$CH$_2$NH$_2$) was suspended in dried CH$_2$Cl$_2$ (25 ml) and Et$_3$N (7 ml), the mixture was sonicated for 30 minutes, and then 4.0 g of chloroacetyl chloride was added at 0° C. under N$_2$. After further refluxed for overnight, the reaction mixture was filtered by using 0.2 μm Millipore nylon membrane filter and repeatedly washed with acetone, DMF, D. I. water and methanol, respectively. 920 g of black solid (MWNT-CONHCH$_2$CH$_2$NHCOCH$_2$Cl) was obtained after dried at room temperature under vacuum.

4) 196.2 mg of (MWNT-CONHCH$_2$CH$_2$NHCOCH$_2$Cl) was mixed with triethyl phosphate (2.36 g) in a vial. After sonicated for 30 minutes, the vial was heated to 150° C. with agitator for 2.5 hours. The cooled reaction mixture was diluted with acetone (40 ml), and then filtered by using 0.2 μm Millipore nylon membrane filter and repeatedly washed with acetone and methanol, respectively. After dried at room temperature under vacuum, 195 mg of black product [MWNT-CONHCH$_2$CH$_2$NHCOCH$_2$PO(OEt)$_2$] was collected.

5) 206 mg of (MWNT-CONHCH$_2$CH$_2$NHCOCH$_2$Cl) was mixed with ethyl diphenylphosphinite (1.33 g) in a vial. After sonicated for 30 minutes, the vial was heated to 150° C. with agitator for 2 hours. The cooled reaction mixture was diluted with acetone (20 ml), and then filtered by using 0.2 μm Millipore nylon membrane filter and repeatedly washed with acetone and methanol, respectively. After dried at room temperature under vacuum, 210 mg of black product [MWNT-CONHCH$_2$CH$_2$NHCOCH$_2$PO(C$_6$H$_5$)$_2$] was collected.

Diethylcarbamoylmethylphosphonate or CMPO Functionalized Single-Wall Carbon Nanotubes 6) 365.2 mg of carboxy-modified single-wall carbon nanotube (SWNT-COOH) was sonicated with a mixture of 55 ml of dried DMF and 12 ml of oxalyl chloride for 30 minutes at 0° C., and then stirred for 8 hours from 0° C. to 70° C. The reaction mixture was evaporated the excess oxalyl chloride to generate carbonyl chloride functional group (SWNT-COCl), which was directly used for next step without further purification.

7) SWNT-COCl in DMF was mixed with ethylenediamine (10.0 g) and placed in an ultrasonic bath for 2 h at room temperature. The mixture was stirred for another 48 h at 90° C. The resulting solid was separated by vacuum filtration using 0.2 μm Millipore nylon membrane filter and repeatedly washed with acetone and methanol, respectively. The resulting solid was dried in a vacuum at room temperature, generating 371 mg of (SWNT-CONHCH$_2$CH$_2$NH$_2$).

8) 70 mg of (SWNT-CONHCH$_2$CH$_2$NH$_2$) was suspended in dried CH$_2$Cl$_2$/DMF (25 ml, 1:4 in v/v) and Et$_3$N (3 ml), the mixture was sonicated for 30 minutes, and then 1.2 g of chloroacetyl chloride was added at room temperature under N$_2$. After further stirred at 80° C. for 24 hours, the reaction mixture was filtered by using 0.2 μm Millipore nylon membrane filter and repeatedly washed with acetone, DMF and methanol, respectively. 72 mg of black solid (SWNT-CONHCH$_2$CH$_2$NHCOCH$_2$Cl) was obtained after dried at room temperature under vacuum.

9) 32 mg of (SWNT-CONHCH$_2$CH$_2$NHCOCH$_2$Cl) was mixed with triethyl phosphate (2.5 ml) in a vial. After sonicated for 30 minutes, the vial was heated to 150° C. with agitator for 3 hours. The cooled reaction mixture was diluted with acetone (20 ml), and then filtered by using 0.2 μm Millipore nylon membrane filter and repeatedly washed with acetone and methanol, respectively. After dried at room temperature under vacuum, 31 mg of black product [SWNT-CONHCH$_2$CH$_2$NHCOCH$_2$PO(OEt)$_2$] was collected.

10) 30 mg of (SWNT-CONHCH$_2$CH$_2$NHCOCH$_2$Cl) was mixed with ethyl diphenylphosphinite (1.5 mL) in a vial. After sonicated for 30 minutes, the vial was heated to 150° C. with agitator for 2.5 hours. The cooled reaction mixture was diluted with acetone (20 ml), and then filtered by using 0.2 μm Millipore nylon membrane filter and repeatedly washed with acetone and methanol, respectively. After dried at room temperature under vacuum, 28 mg of black product [SWNT-CONHCH$_2$CH$_2$NHCOCH$_2$PO(C$_6$H$_5$)$_2$] was collected.

CMPO analogue functionalized multi-wall carbon nanotube (MWNT):

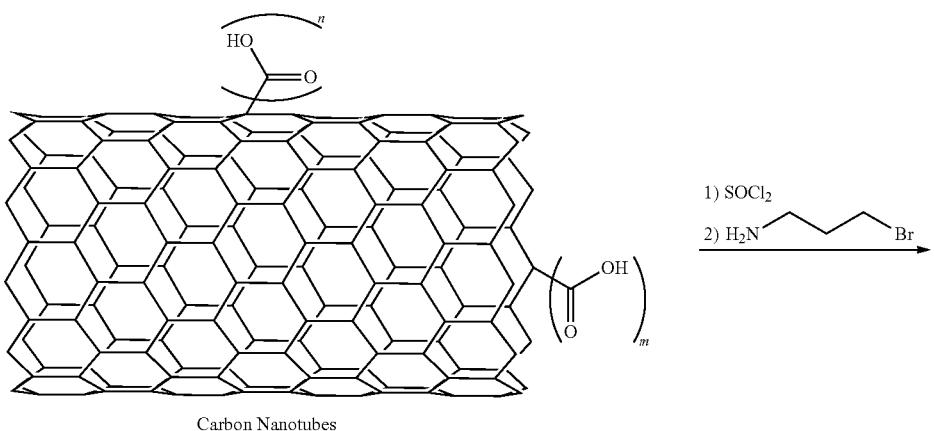

Formula II A

Carbon Nanotubes

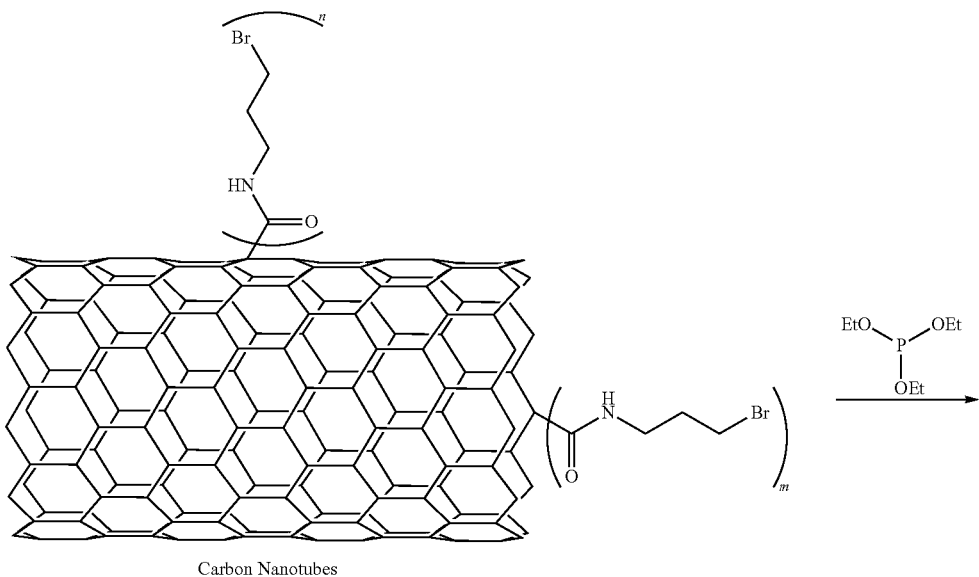

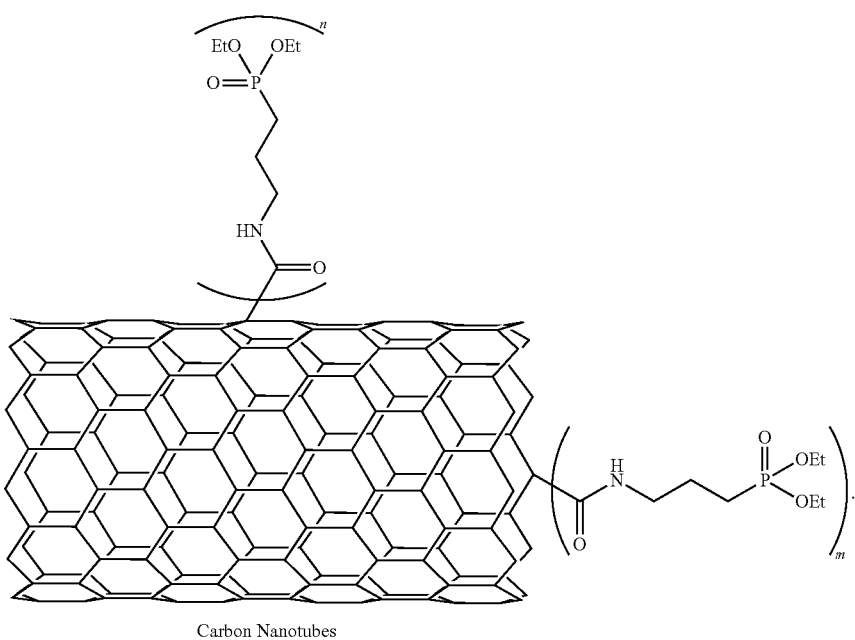

Carbon Nanotubes

1) MWNT-COCl (synthesized from 200 mg of MWNT-COOH) was mixed with 55 ml of DMF, 3-bromopropylamine (1.5 g) and Et$_3$N (2 ml), and then placed in an ultrasonic bath for 2 h at room temperature. The mixture was stirred for another 24 h at 60° C. The resulting solid was separated by vacuum filtration using 0.2 μm Millipore nylon membrane filter and repeatedly washed with acetone and methanol, respectively. The resulting solid was dried in a vacuum at room temperature, generating 209 mg of (MWNT-CONHCH$_2$CH$_2$CH$_2$Br).

2) 199 mg of (MWNT-CONHCH$_2$CH$_2$CH$_2$Br) was mixed with triethyl phosphate (3.18 g) in a vial. After sonicated for 30 minutes, the vial was heated to 160-180° C. with agitator for overnight. The cooled reaction mixture was diluted with acetone (20 ml), and then filtered by using 0.2 μm Millipore nylon membrane filter and repeatedly washed with acetone, THF, DMF and D. I. water, respectively. After dried at room temperature under vacuum, 201 mg of black product [MWNT-CONHCH$_2$CH$_2$CH$_2$PO(OEt)$_2$] was collected.

Phosphate functionalized CNT:

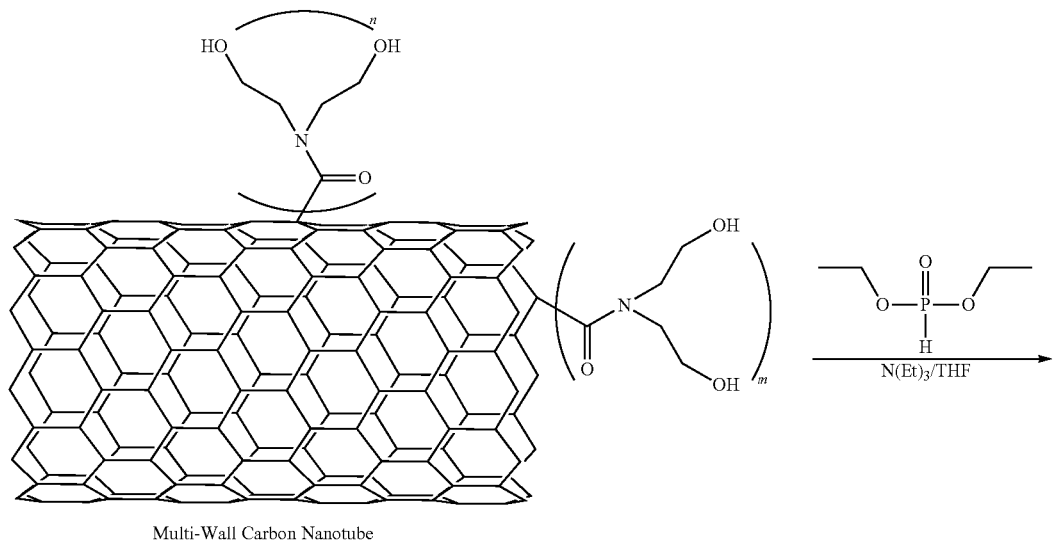

Formula III A

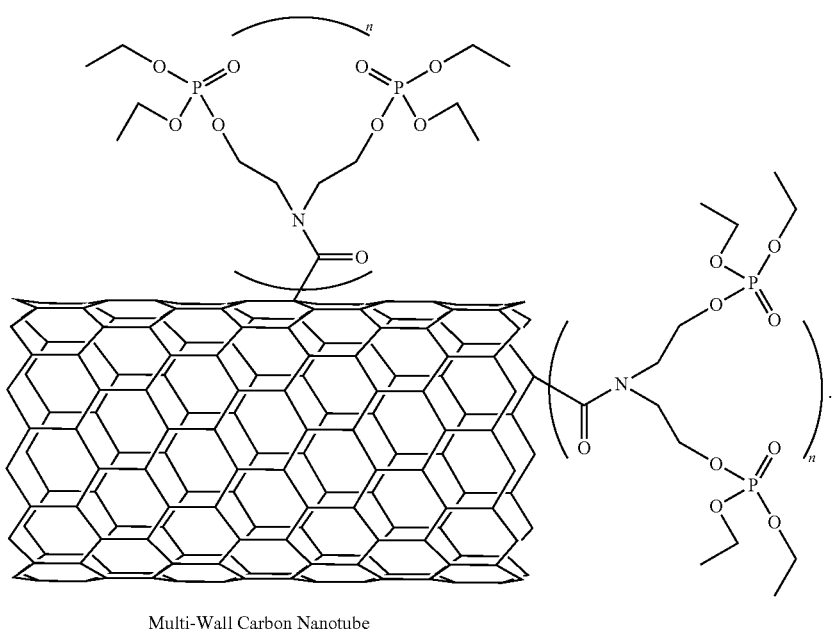

1) MWNT-COCl (synthesized from 300 mg of MWNT-COOH) was mixed with diethanolamine (25 ml) and placed in an ultrasonic bath for 2 h at room temperature. The mixture was stirred for another 3 days at 50° C. The resulting solid was separated by vacuum filtration using 0.2 μm Millipore nylon membrane filter and repeatedly washed with acetone, D. I. water and methanol, respectively. The resulting solid was dried in a vacuum at room temperature, generating 304 mg of [(MWNT-CON(CH$_2$CH$_2$OH)$_2$].

2) 100 mg of [(MWNT-CON(CH$_2$CH$_2$OH)$_2$] in 20 ml DMF was mixed with diethyl phosphite (5 ml), after sonicated for 3 hours, the reaction was heated to 50-90° C. with agitator for 3 hours. The cooled reaction mixture was diluted with acetone (60 ml), and then filtered by using 0.2 μm Millipore nylon membrane filter and repeatedly washed with acetone and methanol, respectively. After dried at room temperature under vacuum, 109 mg of black product {MWNT-CON[CH$_2$CH$_2$OPO(OEt)$_2$]$_2$} was collected.

Diglycolamide functionalized CNT:

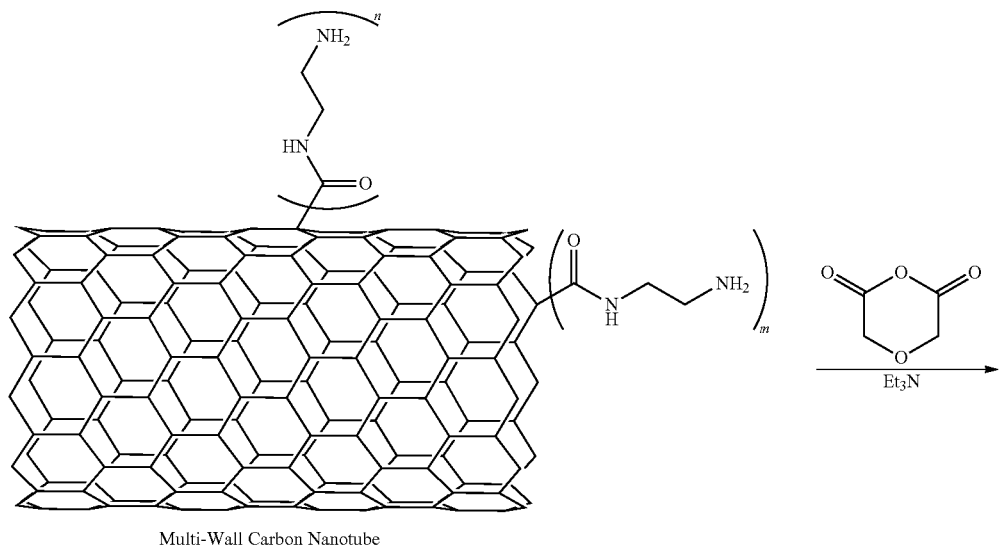

Multi-Wall Carbon Nanotube

Formula VI A

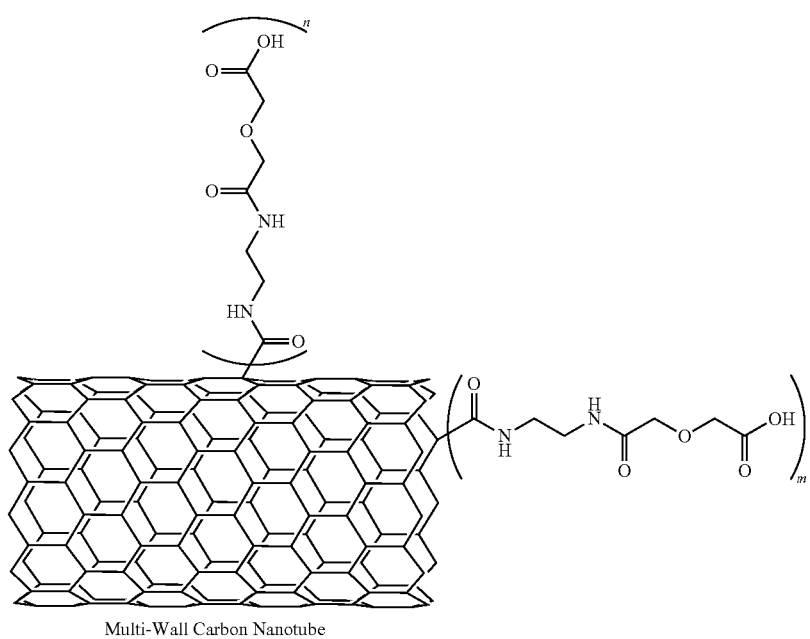

Multi-Wall Carbon Nanotube 153.7 mg of (MWNT-CONHCH$_2$CH$_2$NH$_2$) was mixed with 50 ml of dried THF, Et$_3$N (1 ml) and Diglycolic anhydride (1.195 g), and then placed in an ultrasonic bath for 2 h at room temperature. The mixture was stirred for another 24 h at 80° C. The resulting solid was separated by vacuum filtration using 0.2 μm Millipore nylon membrane filter and repeatedly washed with acetone and methanol, respectively. The resulting solid was dried in a vacuum at room temperature, generating 170 mg of (MWNT-CONHCH$_2$CH$_2$NHCOCH$_2$OCH$_2$COOH).

Cross linked crown ether functionalized CNT:

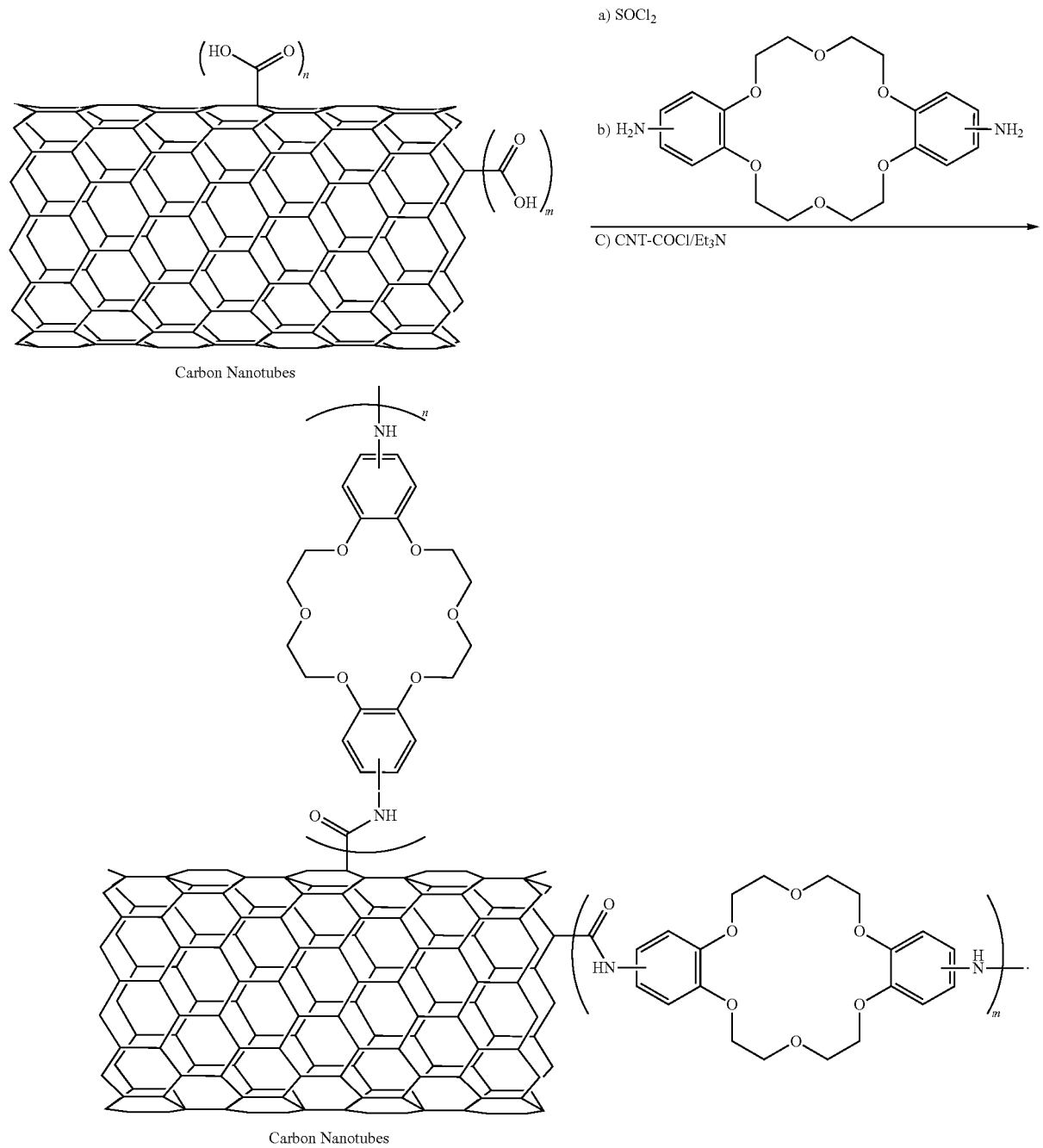

Formula VIII

Carbon Nanotubes

1) MWNT-COCl (synthesized from 200 mg of MWNT-COOH) was mixed with 50 ml of DMF and 1.5 g of di(aminobenzo)-18-crown-6 (J. Am. Chem. Soc. 2000, 122, 6201-6207) and placed in an ultrasonic bath for 2 h at room temperature. The mixture was stirred for another 24 h at 60° C. The resulting solid was separated by vacuum filtration using 0.2 μm Millipore nylon membrane filter and repeatedly washed with acetone and methanol, respectively. The resulting solid was dried in a vacuum at room temperature, 204 mg of [MWNT-(CONHC$_6$H$_3$-18-crown-6-C$_6$H$_3$NH—)$_n$] was collected.

2) 102 mg of [MWNT-(CONHC$_6$H$_3$-18-crown-6-C$_6$H$_3$NH$_2$)$_n$] was sonicated with 45 ml of dried DMF for 1 hour, and then MWNT-COCl (synthesized from 100 mg of MWNT-COOH) was added at room temperature under N$_2$. The reaction mixture was sonicated for another 1 hour, and then stirred at 80° C. for overnight. The product was collected by vacuum filtration using 0.2 μm Millipore nylon membrane filter and repeatedly washed with acetone and methanol, respectively. The resulting solid was dried in a vacuum at room temperature, generating 195 mg of cross linked crown ether functionalized CNT.

Terpyridine functionalized CNT:

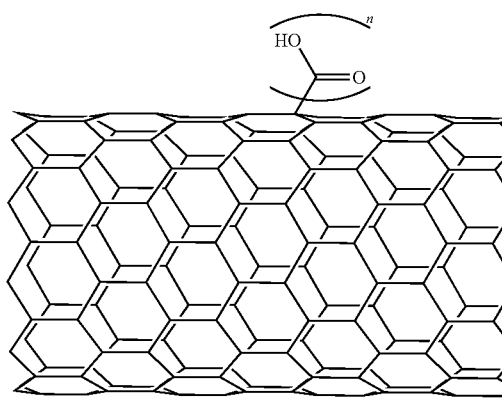

Single-Wall Carbon Nanotube

Formula IX

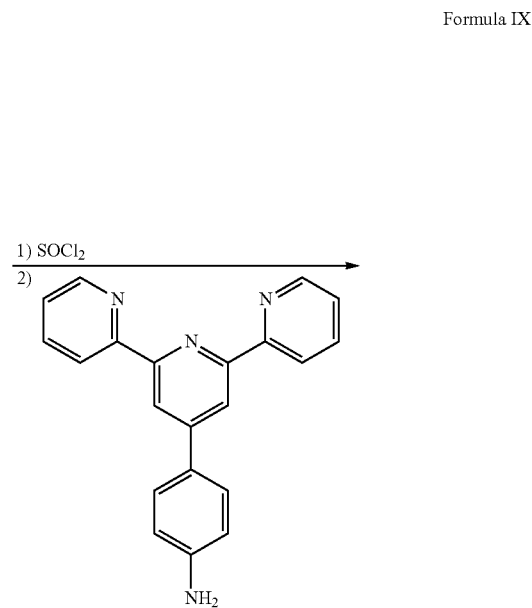

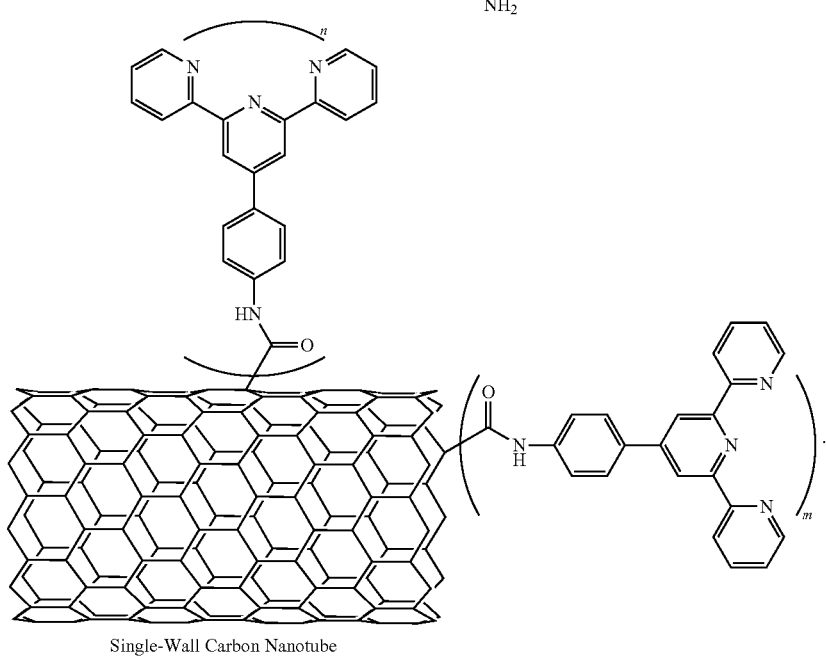

Single-Wall Carbon Nanotube

SWNT-COCl (synthesized from 55 mg of SWNT-COOH) was mixed with 30 ml of DMF, Et$_3$N (0.2 ml) and 4'-(4-Aminophenyl)-2,2':6',2"-Terpyridine (320 mg) and placed in an ultrasonic bath for 2 h at room temperature. The mixture was stirred for another 24 h at 90° C. The resulting solid was separated by vacuum filtration using 0.2 μm Millipore nylon membrane filter and repeatedly washed with acetone and methanol, respectively. The resulting solid was dried in a vacuum at room temperature, generating 59 mg of (MWNT-CONHC$_6$H$_4$-Terpyridine).

General procedure of reacting extractant functionalized carbon nanotubes with metal ions, such as, but not limited to, Ru$^{3+}$ and Eu$^{3+}$, are employed by, for example, mixing 10 mg of extractant functionalized carbon nanotube (for example, MWNT-CONHCH$_2$CH$_2$NHCOCH$_2$OCH$_2$COOH) with 25 ml of D. I. water (or organic solvent, such as DMF or NMP, or mixture of water and organic solvent), above mixture was sonicated at room temperature for 1 hour to make sure to form a homogenous solution; and then metal ion (1.5 mg, such as Eu$_2$(SO$_4$)$_3$ 8H$_2$O) in D. I. water (2 ml) and catalytic amount (10 μl) of reduced reagent (such as N-ethylmorpholine) were added. The reaction mixture was sonicated for 1 hour at 80° C., and then stirred at 80° C. for 8 hours. The black precipitation was collected by vacuum filtration using 0.2 μm Millipore nylon membrane filter and repeatedly washed with acetone, D. I. water and methanol, respectively. The resulting CNT-metal complex was dried in a vacuum at room temperature.

The extractant functionalized carbon nanotubes and CNT-metal complex were characterized by various measurements, such as thermogravimetric analysis (TGA), infrared (IR) and UV-vis spectra, and electron microscopes etc.

What is claimed is:

1. A functionalized carbon nanotube for extracting radionuclides, comprising:
a carbon nanotube containing at least one end functionalized extractant group and at least one surface functionalized extractant group, independently, comprising:
i) a diglycolamide derivative;
ii) a cobalt dicarbollide derivative;

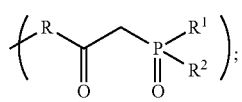

iii)

wherein each R, independently, comprises a) a branched molecule, b) a polymer, c) an amide, d) an alkyl having from 1 to 20 carbon atoms, e) an aryl group f) an aliphatic or an alkyl substituted aryl wherein the aliphatic or alkyl group has from 1 to 20 carbon atoms, or g) a polyethylene glycol having from 2 to 100 ethylene oxide repeat units; and
wherein each $R^1$ and each $R^2$, independently, comprises a) an aryl b) an aliphatic substituted or an alkyl substituted aryl with the aliphatic or alkyl group having from 1 to 20 carbon atoms, or c) an alkoxy group having from 1 to 20 carbon atoms;

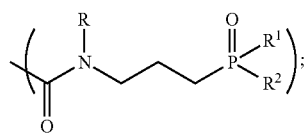

iv)

wherein each R, independently, is a) hydrogen, b) an aliphatic or an alkyl having from 1 to 20 carbon atoms, c) an aryl, d) a substituted aliphatic aryl or an alkyl substituted aryl wherein the aliphatic or alkyl group has from 1 to 20 carbon atoms, or e) a polyethylene glycol having from 2 to 100 ethylene oxide repeat units; and wherein each alkyl group between each phosphine oxide and each amide can be an alkyl having from 1 to 20 carbon atoms; and
wherein each $R^1$ and each $R^2$, independently, is a) an aryl, b) an aliphatic substituted or an alkyl substituted aryl with the aliphatic or alkyl group having from 1 to 20 carbon atoms, c) an alkoxy having from 1 to 20 carbon atoms, or d) an alkyl having from 1 to 20 carbon atoms;

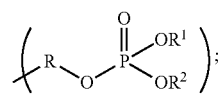

v)

wherein each R, independently, is a) a branched molecule, b) a polymer, c) an amide, d) an alkyl having from 1 to 20 carbon atoms, e) an aryl, f) an aliphatic substituted aryl or an alkyl substituted aryl wherein the aliphatic and the alkyl have from 1 to 20 carbon atoms, or g) a polyethylene glycol having from 2 to 100 ethylene oxide repeat units; and
wherein each $R^1$ and each $R^2$, independently, is a) an aryl, b) an aliphatic substituted aryl or an alkyl substituted aryl wherein the aliphatic and the alkyl group have from 1 to 20 carbon atoms, or c) an alkyl having from 1 to 20 carbon atoms;

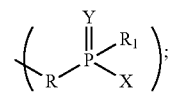

vi)

wherein each R, independently, is a) a branched molecule, b) a polymer, c) an amide, d) an alkyl having from 1 to 20 carbon atoms, e) an aryl f) an aliphatic substituted aryl or an alkyl substituted aryl wherein the aliphatic and the alkyl group having from 1 to 20 carbon atoms, or g) a polyethylene glycol having from 2 to 100 ethylene oxide repeat units; and
wherein each $R^1$, independently, is a) an aryl, (b) an aliphatic substituted or an alkyl substituted aryl wherein the aliphatic and the alkyl group have from 1 to 20 carbon atoms, c) an alkoxy containing from 1 to 20 carbon atoms or d) an alkyl having from 1 to 20 carbon atoms,
wherein X is hydroxy or thio, and
wherein Y is oxygen or sulfur;

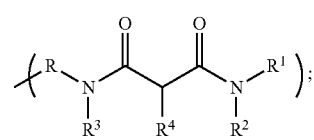

vii)

wherein each R, independently, is a) a branched molecule, b) a polymer, c) an amide, d) an alkyl having from 1 to 20 carbon atoms, e) an aryl, f) an aliphatic substituted or an alkyl substituted aryl wherein the aliphatic or alkyl group contains from 1 to 20 carbon atoms, or g) a polyethylene glycol having from 2 to 100 ethylene oxide repeat units; and
wherein each $R^1$ and each $R^2$, independently, is a) an aryl, b) an aliphatic substituted or an alkyl substituted aryl wherein the aliphatic and the alkyl group has from 1 to 20 carbon atoms, or c) an alkyl having from 1 to 20 carbon atoms; and
wherein each $R^3$ and each $R^4$, independently, is a) a hydrogen, b) an aryl, c) an aliphatic or an alkyl substituted aryl wherein the aliphatic and the alkyl group have from 1 to 20 carbon atoms, or d) an alkyl having from 1 to 20 carbon atoms;

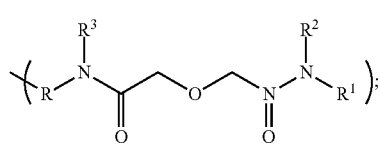

viii)

wherein each R, independently, is a) a branched molecule, b) a polymer, c) an amide, d) an alkyl having from 1 to 20 carbon atoms, e) an aryl, f) an aliphatic substituted or an alkyl substituted aryl wherein the aliphatic or alkyl group contains from 1 to 20 carbon atoms, or g) a polyethylene glycol having from 2 to 100 ethylene oxide repeat units; and wherein each $R^1$ and each $R^2$, independently, is a) a hydrogen, b) an aryl, c) an aliphatic substituted or an alkyl substituted aryl wherein the aliphatic and the alkyl group has from 1 to 20 carbon atoms, or d) an alkyl having from 1 to 20 carbon atoms; and wherein each $R^3$, independently, is a) a hydrogen, b) an aryl, c) aliphatic or an alkyl substituted aryl wherein the aliphatic and the alkyl group having from 1 to 20 carbon atoms, or d) an alkyl having from 1 to 20 carbon atoms;

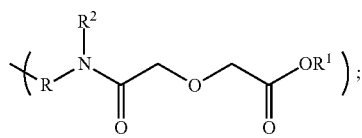

ix)

wherein each R, independently, is a) a branched molecule, b) a polymer, c) an amide, d) an alkyl having from 1 to 20 carbon atoms, e) an aryl, f) an aliphatic substituted or an alkyl substituted aryl wherein the aliphatic or alkyl group contains from 1 to 20 carbon atoms, or g) a polyethylene glycol having from 2 to 100 ethylene oxide repeat units; and wherein $R^1$ is a) hydrogen, b) an aryl, c) an aliphatic substituted or an alkyl substituted aryl wherein the aliphatic and the alkyl group has from 1 to 20 carbon atoms, or d) an alkyl having from 1 to 20 carbon atoms; and wherein said $R^2$ is a) hydrogen, b) an aryl, c) an aliphatic or an alkyl substituted aryl wherein the aliphatic and the alkyl group have from 1 to 20 carbon atoms, or d) an alkyl having from 1 to 20 carbon atoms;

or any combinations of said i) through ix) thereof; and wherein said carbon nanotube is a single-wall nanotube, a double-wall nanotube, a multi-wall nanotube, or a carbon nanohorn, or combinations thereof.

2. The functionalized carbon nanotube of claim 1, wherein said functionalized carbon nanotube is capable of extracting radionuclides, or an actinide, or a lanthanide, or combinations thereof.

3. The functionalized carbon nanotube of claim 1, wherein said end functionalized extractant group is said iii)

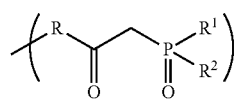

and wherein said surface functionalized extractant group is said iii)

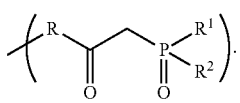

4. The functionalized carbon nanotube of claim 1, wherein said end functionalized extractant group is said iv)

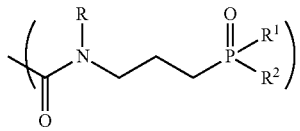

and wherein said surface functionalized extractant group is said iv)

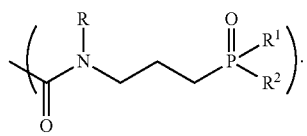

5. The functionalized carbon nanotube of claim 1, wherein said end functionalized extractant group is said v)

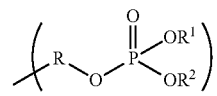

and wherein said surface functionalized extractant group is said v)

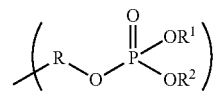

wherein each R, independently, is a) a branched molecule, c) a polymer, d) an amide, e) an alkyl having from 1 to about 20 carbon atoms, f) an aryl, g) an aliphatic substituted aryl or an alkyl substituted aryl wherein the aliphatic and the alkyl have from 1 to about 20 carbon atoms, or h) a polyethylene glycol having from 2 to about 100 ethylene oxide repeat units; and wherein each $R^1$ and each $R^2$, independently, is a) an aryl, b) an aliphatic substituted aryl or an alkyl substituted aryl wherein the aliphatic and the alkyl group have from about 1 to about 20 carbon atoms, or c) an alkyl having from 1 to about 20 carbon atoms.

6. The functionalized carbon nanotube of claim 1, wherein said end functionalized extractant group is said vi)

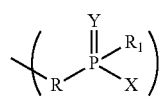

and wherein said surface functionalized extractant group is said vi)

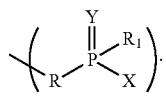

7. The functionalized carbon nanotube of claim 1, wherein said end functionalized extractant group is said vii)

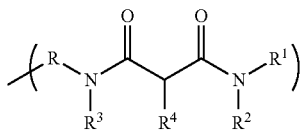

and wherein said surface functionalized extractant group is said vii)

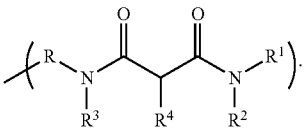

8. The functionalized carbon nanotube of claim 1, wherein said end functionalized extractant group is said viii)

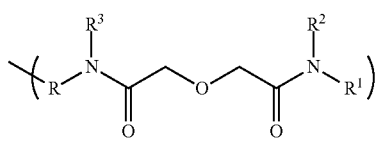

and wherein said surface functionalized extractant group is said viii)

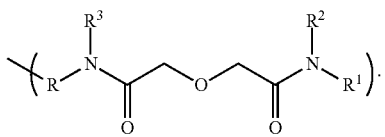

9. The functionalized carbon nanotube of claim 1, wherein said end functionalized extractant group is said ix)

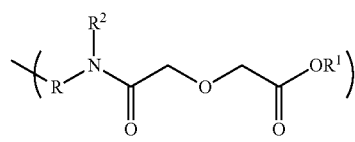

and wherein said surface functionalized extractant group is said ix)

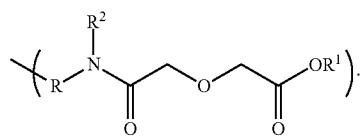

10. The functionalized carbon nanotube of claim 1, wherein each said functionalized extractant group is a N-donating heterocyclic group that is nitrogen incorporated into the mono- and polytopic aromatic ring.

11. A functionalized carbon nanotube, comprising:
a carbon nanotube having a functional group thereon, the functional group including a phosphine oxide derivative, a phosphoric acid derivative, a diglycolamide derivative, or a cobalt dicarbollide derivative or a combination thereof;
wherein said carbon nanotube is one or more of a single-wall nanotube, a double-wall nanotube, a multi-wall nanotube, and a carbon nanohorn;
wherein the phosphine oxide derivative has the formula:

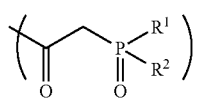

wherein $R^1$ and $R^2$, independently, comprise a) an aryl, b) an aliphatic substituted or an alkyl substituted aryl with the aliphatic or alkyl group having from 1 to 20 carbon atoms, or c) an alkoxy group having from 1 to 20 carbon atoms; or wherein the phosphine oxide derivative has the formula:

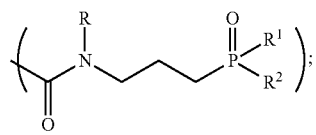

wherein each R, independently, is a) hydrogen, b) an aliphatic or an alkyl having from 1 to 20 carbon atoms, c) an aryl, d) a substituted aliphatic aryl or an alkyl substituted aryl wherein the aliphatic or alkyl group has from 1 to 20 carbon atoms, or e) a polyethylene glycol having from 2 to 100 ethylene oxide repeat units; wherein the alkyl group between phosphine oxide and amide is an alkyl having from 1 to 20 carbon atoms; and wherein $R^1$ and $R^2$, independently, is a) an aryl, b) an aliphatic substituted or an alkyl substituted aryl with the aliphatic or alkyl group having from 1 to 20 carbon atoms, c) an alkoxy having from 1 to 20 carbon atoms, or d) an alkyl having from 1 to 20 carbon atoms; or wherein the phosphine oxide derivative has the formula:

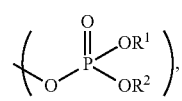

wherein $R^1$ and $R^2$, independently, is a) an aryl, b) an aliphatic substituted aryl or an alkyl substituted aryl wherein the aliphatic and the alkyl group have from 1 to 20 carbon atoms, or c) an alkyl having from 1 to 20 carbon atoms;

wherein the phosphoric acid derivative has the formula:

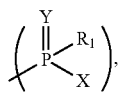

wherein $R_1$, independently, is a) an aryl, b) an aliphatic substituted or an alkyl substituted aryl wherein the aliphatic and the alkyl group having from 1 to 20 carbon atoms, c) an alkoxy containing from 1 to 20 carbon atoms, or d) an alkyl having from 1 to 20 carbon atoms, wherein X is hydroxy or thio, and wherein Y is oxygen or sulfur.

12. The functionalized carbon nanotube of claim 11, wherein the phosphine oxide derivative has the formula:

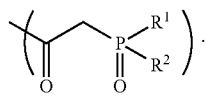

13. The functionalized carbon nanotube of claim 11, wherein the phosphine oxide derivative has the formula:

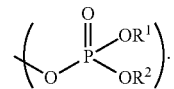

14. The functionalized carbon nanotube of claim 11, wherein the phosphine oxide derivative has the formula:

15. The functionalized carbon nanotube of claim 11, wherein the phosphoric acid derivative has the formula:

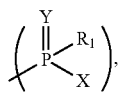

16. A functionalized carbon nanotube, comprising: a carbon nanotube having a functional group thereon, wherein the functionalized carbon nanotube is an acetamidophosphine oxide functionalized carbon nanotube, or a diethylcarbamoylmethylphosphonate functionalized carbon nanotube.

* * * * *